US009820955B2

(12) United States Patent
Kaufman et al.

(10) Patent No.: US 9,820,955 B2
(45) Date of Patent: Nov. 21, 2017

(54) GABA AGONISTS IN THE TREATMENT OF DISORDERS ASSOCIATED WITH METABOLIC SYNDROME AND GABA COMBINATIONS IN TREATMENT OR PROPHYLAXIS OF TYPE I DIABETES

(71) Applicant: The Regents of the University of California, Oakland, CA (US)

(72) Inventors: Daniel Kaufman, Los Angeles, CA (US); Jide Tian, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/752,487

(22) Filed: Jun. 26, 2015

(65) Prior Publication Data

US 2016/0081956 A1    Mar. 24, 2016

Related U.S. Application Data

(62) Division of application No. 13/876,147, filed as application No. PCT/US2011/053732 on Sep. 28, 2011, now Pat. No. 9,089,531.

(60) Provisional application No. 61/387,398, filed on Sep. 28, 2010, provisional application No. 61/433,089, filed on Jan. 14, 2011.

(51) Int. Cl.
| *A61K 31/135* | (2006.01) |
| *A61K 31/197* | (2006.01) |
| *A61K 31/4465* | (2006.01) |
| *A61K 45/06* | (2006.01) |
| *A61K 38/20* | (2006.01) |
| *A61K 39/00* | (2006.01) |
| *A61K 39/39* | (2006.01) |

(52) U.S. Cl.
CPC ........ *A61K 31/197* (2013.01); *A61K 31/4465* (2013.01); *A61K 38/2013* (2013.01); *A61K 39/0008* (2013.01); *A61K 39/39* (2013.01); *A61K 45/06* (2013.01)

(58) Field of Classification Search
CPC . A61K 38/2013; A61K 39/0008; A61K 39/39
See application file for complete search history.

(56) References Cited

U.S. PATENT DOCUMENTS

| 6,207,159 | B1 | 3/2001 | Kaufman et al. |
| 6,350,769 | B1 | 2/2002 | Kaufman et al. |
| 9,089,531 | B2 | 7/2015 | Kaufman et al. |
| 2003/0162754 | A1 | 8/2003 | Ligon |
| 2003/0170239 | A1 | 9/2003 | Hering et al. |
| 2007/0128298 | A1 | 6/2007 | Cowley et al. |
| 2008/0226716 | A1 | 9/2008 | Gallop et al. |
| 2008/0255093 | A1 | 10/2008 | Tam et al. |
| 2010/0166675 | A1 | 7/2010 | Wang et al. |
| 2010/0197789 | A1 | 8/2010 | Arima et al. |
| 2013/0251671 | A1 | 9/2013 | Kaufman et al. |

FOREIGN PATENT DOCUMENTS

| WO | JP 2009298742 A | 12/2009 |
| WO | WO 2012/050907 | 4/2012 |

OTHER PUBLICATIONS

PCT International Search Report and Written Opinion dated May 1, 2012 issued in PCT/US2011/053732.
PCT International Preliminary Report on Patentability dated Apr. 2, 2013 issued in PCT/US2011/053732.
CN Office Action dated Sep. 18, 2014 in CN 201180057204.3.
CN Second Office Action dated Jul. 27, 2015 in CN 201180057204.3.
CN Decision on Rejection dated Apr. 5, 2016 in CN 201180057204.3.
CN Notification of Reexamination dated Jan. 10, 2017 in CN 201180057204.3.
EP Extended Search Report dated Apr. 9, 2014 issued in EP 11833060.4-1466.
EP Office Action dated Feb. 2, 2016 issued in EP 11833060.4-1466.
EP Office Action dated Mar. 30, 2017 issued in EP 11833060.4-1466.
U.S. Office Action [Restriction Requirement] dated Aug. 2, 2013 issued in U.S. Appl. No. 13/876,147.
U.S. Office Action dated Jan. 21, 2014 issued in U.S. Appl. No. 13/876,147.
U.S. Notice of Allowance dated Mar. 23, 2015 issued in U.S. Appl. No. 13/876,147.
Blasi (2000) "Influence of Benzodiazepines on Body Weight and Food Intake in Obese and Lean Zucker Rats," *Prog. Neuro-Psychopharmacol. & Biol. Psychiat*, 24(4): 561-577.
Chatenoud et al. (1994) "Anti-CD3 antibody induces long-term remission of overt autoimmunity in nonobese diabetic mice" *Proc. Natl. Acad. Sci., U.S.A.* 91: 123-127.

(Continued)

*Primary Examiner* — Prema Mertz
(74) *Attorney, Agent, or Firm* — Tom Hunter; Weaver Austin Villeneuve & Sampson LLP

(57) ABSTRACT

In certain embodiments methods are provided for the therapeutic or prophylactic amelioration of one or more symptoms or disorders associated with metabolic syndrome. In various embodiments the methods involve administering to a subject in need thereof, a GABA receptor agonist, in an amount sufficient to ameliorate said one or more symptoms. In certain embodiments methods are provided for the prophylaxis or treatment of type I diabetes and related pathologies that involve the use of GABA or GABA agonists in combination with certain other compounds (e.g., one more antigens (e.g., GAD) that have a therapeutic effect in type I diabetes and/or an anti-CD3 antibody, an anti-CD20 antibody, exendin-4, and/or or a pro-insulin therapeutic).

15 Claims, 14 Drawing Sheets

(56) References Cited

OTHER PUBLICATIONS

Devraj, et al. (Apr. 15, 2008) "CRP and Adiponectin and Its Oligomers in the Metabolic Syndrome: Evaluation of New Laboratory-Based Biomarkers," *American Journal of Clinical Pathology*, 129(5): 815-822.

Diamyd shows efficacy in type I diabetes trial. (2006) *ESPICOM Pharmaceutical and Medical Device News*, Retrieved from http://search.proquest.com/professional/docview/765061162?accountid=162131.

Gerling et al. (1992) "Intrathymic Islet Cell Transplantation Reduces Beta-Cell Autoimmunity and Prevents Diabetes in NOD/Lt Mice." *Diabetes*, 41: 1672-1676.

Goudy et al. (2005) "Immunotherapy for the Prevention and Treatment of Type 1 Diabetes" *International Reviews of Immunology* 24:307-326.

Grinberg-Bleyer et al. (2010) "IL-2 reverses established type 1 diabetes in NOD mice by a local effect on pancreatic regulatory T cells" *J. Exp. Med.* 207: 1871-1878.

Grundy, Scott (Feb. 14, 2012) "Pre-Diabetes, Metabolic Syndrome, and Cardiovascular Risk" *Journal of the American College of Cardiology* 59(7): 635-643.

Hagiwara, et al. (2004) "The Effect of Pre-germinated Brown Rice Intake on Blood Glucose and PAI-1 Levels in Streptozotocin-induced Diabetic Rats," *Bioscience. Biotechnology. And Biochemistry*, 68(2): 444-447.

Hu et al. (2007) "Treatment with CD20-specific antibody prevents and reverses autoimmune diabetes in mice." *Journal of Clinical Investigation* 117(12): 3857-3867.

Kazama, et al. (Jun. 1, 2010) "Oral administration of GABA and phytosteryl ferulates prevent decreasing stressed mouse plasma adiponectin levels," *FEBS Journal—A3 Metabolic Diseases* [XP009177205], 277(Supp 1): 70-71, Abstract: A3.57.

Maki et al. (1992) "Long-term abrogation of autoimmune diabetes in nonobese diabetic mice by immunotherapy with anti-lymphocyte serum" *Proc. Natl. Acad. Sci., U.S.A.* 89: 3434-3438.

Ohara, et al. (Jun. 15, 2011) "Oral administration of γ-aminobutyric acid and γ-oryzanol prevents stress-induced hypoadiponectinemia," *Phytomedicine*, 18(8):655-660.

Parker et al. (2009) "Immune Depletion With Cellular Mobilization Imparts Immunoregulation and Reverses Autoimmune Diabetes in Nonobese Diabetic Mice" *Diabetes*, 58: 2277-2284.

Saas, et al. (2005) "Nonalcoholic Fatty Liver Disease: A Clinical Review," *Digestive Diseases and Sciences*, 50(1): 171-180.

Saely, et al. (Jul. 4, 2007) "Low serum adiponectin is independently associated with both the metabolic syndrome and angiographically determined coronary atherosclerosis," *Clinica Chimica Acta*, 383(1-2):97-102.

Sherry et al. (2007) "Exendin-4 Improves Reversal of Diabetes in NOD Mice Treated with Anti-CD3 Monoclonal Antibody by Enhancing Recovery of β-Cells" *Endocrinology* 148(11): 5136-5144.

Song et al. (2004) "Recombinant adena-associated virus-mediated alpha-1 antitrypsin gene therapy prevents type I diabetes in NOD mice." *Gene Therapy*, 11: 181-186.

Squadrito, et al. (Dec. 1, 1988) "Evidence that a gabaergic mechanism influences the development of obesity in obese zucker rats," *Pharmacological Research Communications*, 20(12): 1087-88.

Tews, et al. (Dec. 14, 1981) "Dietary GABA decreases body weight of genetically obese mice," *Life Sciences*, 29(24): 2535-2542.

Tian et al. (2004) "Gamma-Aminobutyric Acid Inhibits T Cell Autoimmunity and the Development of Inflammatory Responses in a Mouse Type 1 Diabetes Model" *Journal of Immunology* 173: 5298-5304.

Tian et al. (2011) "Oral Treatment with γ-Aminobutyric Acid Improves Glucose Tolerance and Insulin Sensitivity by Inhibiting Inflammation in High Fat Diet-Fed Mice" *PLoS ONE* 6(9): e25338(7 pages).

Tian, et al. (Sep. 2014) "Combined Therapy With GABA and Proinsulin/Alum Acts Synergistically to Restore Long-term Normoglycemia by Modulating T-Cell Autoimmunity and Promoting β-Cell Replication in Newly Diabetic NOD Mice," *Diabetes* 63: 3128-3134.

Turvey et al. (2005) "Noninvasive imaging of pancreatic inflammation and its reversal in type 1 diabetes" *J. Clin. Invest.*, 115: 2454-2461.

Uchida, et al. (Jun. 28, 2008) "Effect of rice germ on plasma adiponectin level in C57BL/6j mice," *FEBS Journal—8. Applied Biochemistry and Biotechnology* [XP009177219], 275(Supp 1): 434, Abstract: PP8.191.

Xu et al. (2006) "Intra-islet insulin suppresses glucagon release via GABA-GABM receptor system" *Cell Metabolism* 3(1): 47-58.

GABA AGONISTS IN THE TREATMENT OF DISORDERS ASSOCIATED WITH METABOLIC SYNDROME AND GABA COMBINATIONS IN TREATMENT OR PROPHYLAXIS OF TYPE I DIABETES

CROSS-REFERENCE TO RELATED APPLICATIONS

This application is a Divisional of U.S. Ser. No. 13/876,147, filed on Jun. 10, 2013, which is a U.S. 371 National Phase of PCT/US2011/053732, filed on Sep. 28, 2011, which claims benefit of and priority to U.S. Ser. No. 61/387,398, filed on Sep. 28, 2010, and to U.S. Ser. No. 61/433,089, filed Jan. 14, 2011, all of which are incorporated herein by reference in their entirety for all purposes.

STATEMENT OF GOVERNMENTAL SUPPORT

This work was supported in part by Grant No DK075070 awarded by the National Institutes of Health. The government has certain rights in this invention.

BACKGROUND OF THE INVENTION

Type I, or insulin-dependent, diabetes mellitus is known to occur spontaneously in humans, rats and mice (Castao and Eisenbarth (1990) Ann. Rev. Immunol. 8:647-679). There is a genetic susceptibility to type I diabetes associated with certain haplotypes of Class II antigens of the major histocompatability complex (MHC), i.e., HLA-DR3, -DR4 and -DQ3.2 in humans (see e.g., Platz et al. (1981) Diabetologia 21:108-115; Todd et al. (1987) Nature 329:599-604); $RT1^u$ in Bio-Breeding (BB) rats (see e.g., Colle (1990) Clin. Immunol. & Immunopathol. 57: 1-9; Parfrey et al. (1989) Crit. Rev. Immunol. 9: 45-65) and $H-2^{g7}$ in non-obese diabetic (NOD) mice (see e.g., Kikutani and Makino in Adv. Immunol. (Dixon, F. J., ed.), pp. 285-323, New York, N.Y.: Academic Press, Inc., 1992). The pathology of type I diabetes involves the progressive inflammatory infiltration of pancreatic islets (i.e., insulitis) containing immunocytes targeted specifically to insulin-secreting β-cells (see e.g., Bottazzo et al. (1985) N. Eng. J. Med. 313: 353-360; Foulis et al. (1991) J. Pathol. 165: 97-103; Hanenberg et al. (1991) Diabetologia 32: 126-134). This pathology develops over an indeterminate period of time (months to years).

Over one half million people in the United States suffer from insulin-dependent diabetes. Prior to 1921, people who developed type I diabetes were not expected to live much more than a year after diagnosis. Afflicted individuals suffered from clinical signs of chronic hyperglycemia (e.g., excessive thirst and urination, rapid weight loss) as a consequence of abnormal carbohydrate metabolism. Once insulin was purified and administered, the life-expectancy of diabetics increased dramatically. However, type I diabetes is a chronic disease that requires life-long treatment to prevent acute illness and to reduce the risk of long-term complications. Restrictive diets and daily insulin injections can be burdensome for patients, thus reducing compliance, and even with treatment complications such as cataracts, retinopathy, glaucoma, renal disease and circulatory disease are prevalent.

Metabolic syndrome is a group of risk factors characterized by impaired glucose tolerance, reduced insulin sensitivity, hypertension, hyperlipidemia, obesity and chronic inflammation. Inflammation is thought to be involved since a number of inflammatory molecules as IL-6, TNFα and C-reactive protein are increased. Individuals with metabolic disease have higher risk for cardiovascular diseases, heart attack, stroke, type 2 diabetes (T2D) and nonalcoholic liver disease.

SUMMARY OF THE INVENTION

In certain embodiments a method method of ameliorating one or more symptoms or disorders associated with metabolic syndrome is provided. The method typically involves administering, or causing to be administered, to a mammal in need thereof GABA, and/or a GABA receptor agonist, and/or a GABA potentiator, and/or a GABA prodrug and/or a GABA agonist prodrug in an amount sufficient to ameliorate said one or more symptoms. In certain embodiments the symptoms or disorders comprise insulin resistance, and/or glucose intolerance, and/or hypertension, and/or fatty liver disease, and/or macrophage infiltrates into adipose tissue, and/or chronic kidney disease, and/or obesity.

In certain embodiments a method of slowing or stopping the progression from a pre-diabetic condition in a mammal or from a non-diabetic condition in a mammal at risk for type II diabetes to type II diabetes. The method typically involves administering to said mammal GABA, and/or a GABA receptor agonist, and/or a GABA potentiator, and/or a GABA prodrug and/or a GABA agonist prodrug, in an amount sufficient to slow or stop progression of the mammal from a pre-diabetic or a non-diabetic condition to type II diabetes.

Also provided is a composition comprising GABA, and/or a GABA receptor agonist, and/or a GABA potentiator, and/or a GABA prodrug and/or a GABA agonist prodrug receptor agonist for use in: ameliorating one or more symptoms or disorders associated with metabolic syndrome; and/or slowing or stopping the progression from a pre-diabetic condition in a mammal or from a non-diabetic condition in a mammal at risk for type II diabetes to type II diabetes.

In certain embodiments in any of the foregoing methods and/or compositions the composition comprises GABA and/or the composition administered is GABA. In certain embodiments in any of the foregoing methods and/or compositions the GABA agonist is a $GABA_A$-specific agonist and/or $GABA_A$ preferential and/or a $GABA_B$-specific and/or a $GABA_B$-preferential agonist. In certain embodiments in any of the foregoing methods and/or compositions the GABA receptor agonist comprises a compound selected from the group consisting of thiopental, thiamylal, pentobarbital, secobarbital, hexobarbital, butobarbital, amobarbital, barbital, mephobarbital, phenobarbital, primidone, midazolam, triazolam, lometazepam, flutazolam, nitrazepam, fluritrazepam, nimetazepam, diazepam, medazepam, oxazolam, prazeam, tofisopam, rilmazafonoe, lorazepam, temazepam, oxazepam, fluidazepam, chlordizaepoxide, cloxazolam, flutoprazepam, alprazolam, estazolam, bromazepam, flurazepam, clorazepate potassium, haloxazolam, ethyl loflazepate, qazepam, clonazepam, mexazolam, etizolam, brotizolam, clotizaepam, propofol, fospropofol, zolpidem, zopiclone, and exzopiclone. In certain embodiments in any of the foregoing methods and/or compositions the GABA receptor agonist comprises a compound is selected from the group consisting of muscimol, THIP/gaboxadol, Isoguvacine, Kojic amine, GABA, Homotaurine, Homohypotaurine, Trans-aminocyclopentane-3-carboxylic acid, Trans-amino-4-crotonic acid, β-guanidinopropionic acid, homo-β-proline, Isonipecotic acid, 3-((aminoiminomethyl)thio)-2-propenoic acid (ZAPA), Imidazoleacetic acid, and piperidine-4-sulfonic acid (P4S). In certain embodiments the GABA receptor agonist is not a barbituate, and/or not a benzodiazepine, and/or not a thienodiazepine, and/or not a dialkylphenol. In certain embodiments the compound (active agent) is not GABA. In certain embodiments in any of the foregoing methods and/or compositions the mammal is a mammal diagnosed as obese or pre-obese or at risk for obesity. In certain embodiments in any of the foregoing methods and/or compositions the mammal is a mammal diagnosed as diabetic or pre-diabetic. In certain embodiments in any of the foregoing methods and/or compositions the mammal is diagnosed as having or at risk for type II diabetes. In certain embodiments the mammal is a human or a non-human mammal. In certain embodiments the compound is not an agonist at the $GABA_B$ receptor. In certain embodiments the compound is not an agonist at the $GABA_A$ receptor. In certain embodiments in any of the foregoing methods and/or compositions the mammal is not a mammal diagnosed as having or at risk for one or more conditions selected from the group consisting of a sleep disorder or insomnia, CNS disorder (e.g., muscle relaxation in spinal spasticity), a cardiovascular disorder, asthma, a gut motility disorder (e.g., irritable bowel syndrome), a subject being treated with a prokinetic and/or anti-tussive agents, a subject treated for emesis, a subject diagnosed as having or at risk for an autoimmune disease (e.g., rheumatoid arthritis), a subject diagnosed as having or at risk for a neurophysiological or neurophsychiatric disorder, a subject as having or at risk for a psychiatric disorder (e.g., anxiety and/or depression), a subject diagnosed as having or at risk spasticity/muscle spasms, a subject diagnosed as having or at risk for Huntington's disease and/or Parkinson's disease, and/or a subject having or at risk for MS.

In certain embodiments methods involving the coadministration of GABA and/or GABA agonists in combination with a second active agent are contemplated. In certain embodiments a method of delaying the onset of type I diabetes, and/or slowing the progression of type I diabetes, and/or reducing the severity of type I diabetes, and/or reversing type I diabetes in a mammal in a mammal is provided. The method typically involves coadministering to said mammal a first compound (or composition) comprising GABA, a GABA analogue/agonist, and/or a GABA prodrug and/or A GABA agonist prodrug; and a second compound (or composition) comprising a non-GABA therapeutic agent for the treatment of type I diabetes, and/or an anti-inflammatory compound, and/or a factor that stimulates a regulatory or immune response, and/or a $GABA_B$ receptor agonist, where the first compound and the second compound are administered in an amount sufficient to delay the onset of type I diabetes, and/or slow the progression of type I diabetes, and/or reduce the severity of type I diabetes, and/or reverse type I diabetes in said mammal. In certain embodiments a method of delaying the onset of hyperglycemia, and/or slowing the progression of hyperglycemia, and/or reducing the severity of hyperglycemia, and/or reversing hyperglycemia in a mammal, is provided. The method typically involves coadministering to the mammal a first compound (or composition) comprising GABA, a GABA analogue, a GABA agonist, and/or a GABA or GABA agonist prodrug; and a second compound (or composition) comprising a non-GABA therapeutic agent for the treatment of type I diabetes, and/or an anti-inflammatory compound, and/or a factor that stimulates a regulatory or immune response, and/or a $GABA_B$ receptor agonist, where the first compound and the second compound are administered in an amount sufficient to delay the onset of hyperglycemia, and/or slow the progression of hyperglycemia, and/or to reduce the severity of hyperglycemia, and/or to reverse hyperglycemia in said mammal. In certain embodiments a method of promoting transplanted islet cell survival in a mammal having Type I diabetes or at risk for type I diabetes who is a recipient of transplanted islet cells is provided. The method typically involves coadministering to the mammal a first compound (or composition) comprising GABA, a GABA analogue, a GABA agonist, and/or a GABA or GABA agonist prodrug; and a second compound (or composition) comprising a non-GABA therapeutic agent for the treatment of type I diabetes, and/or an anti-inflammatory compound, and/or a factor that stimulates a regulatory or immune response, and/or a $GABA_B$ receptor agonist; where the first compound (or composition) and the second compound (or composition) are administered in an amount sufficient to promote transplanted islet cell survival in said mammal.

In certain embodiments a method of delaying the onset of an immune response, and/or slowing the progression of an immune response, and/or reducing the severity of an immune response, and/or suppressing an immune response in a mammal is provided. The method typically involves coadministering to the mammal a first compound (or composition) comprising GABA, a GABA analogue, a GABA agonist, a GABA or GABA agonist prodrug, and/or a GABA potentiator; and a second compound (or composition) comprising a non-GABA therapeutic agent for the treatment of type I diabetes, and/or an anti-inflammatory compound, and/or a factor that stimulates a regulatory or immune response, and/or a $GABA_B$ receptor agonist, where the first compound and the second compound are administered in an amount sufficient to delay the onset of an immune response, and/or slow the progression of an immune response, and/or reduce the severity of an immune response, and/or suppress an immune response in the mammal.

In certain embodiments a method of protecting beta-cells in a mammal from oxidative stress induced apoptosis is provided. The method typically involves coadministering to a mammal containing said β-cells a first compound (composition) comprising GABA, a GABA analogue, a GABA agonist, a GABA or GABA agonist prodrug, and/or a GABA potentiator; and a second compound (composition) comprising a non-GABA therapeutic agent for the treatment of type I diabetes, and/or an anti-inflammatory compound, and/or a factor that stimulates a regulatory or immune response, and/or a $GABA_B$ receptor agonist, where the first compound and said second compound are administered in an amount sufficient to partially or fully protect said beta cells from oxidative stress induced apoptosis.

In various embodiments a combination of compounds for use in the various indicates described above (and further below herein) is provided. Accordingly, in certain embodiments first compound comprising GABA, a GABA analogue, a GABA agonist, and/or a GABA or GABA agonist prodrug; and a second compound comprising a non-GABA therapeutic agent for the treatment of type I diabetes, and/or an anti-inflammatory compound, and/or a factor that stimulates a regulatory or immune response, and/or a $GABA_B$ receptor agonist for use in conjunction with each other to delay the onset of type I diabetes, and/or slow the progression of type I diabetes, and/or reduce the severity of type I diabetes, and/or reverse type I diabetes in a mammal; and/or to promote transplanted islet cell survival in a mammal; and/or to delay the onset of hyperglycemia, and/or to slow the progression of hyperglycemia, and/or to reduce the severity of hyperglycemia, and/or to reverse hyperglycemia in a mammal; and/or to promote transplanted islet cell survival in a mammal having type I diabetes or at risk for type I diabetes who is a recipient of transplanted islet cells; and/or to delay the onset of an immune response, and/or slow the progression of an immune response, and/or reduce the severity of an immune response, and/or suppress an immune response in a mammal; and/or to protect beta-cells in a mammal from oxidative stress induced apoptosis is provided.

Also provided is a kit comprising a first container containing a first compound comprising GABA, and/or a GABA analogue, and/or a GABA agonist, and/or a GABA or GABA agonist prodrug; and a second container containing a non-GABA therapeutic agent for the treatment of type I diabetes, and/or an anti-inflammatory compound, and/or a factor that stimulates a regulatory or immune response, and/or a $GABA_B$ receptor agonist.

Additionally, "combination" pharmaceuticl formulations are provided. In certain embodiments the formulation comprises GABA, a GABA analogue, a GABA agonist, and/or a GABA or GABA agonist prodrug; and a non-GABA therapeutic agent for the treatment of type I diabetes, and/or an anti-inflammatory compound, and/or a factor that stimulates a regulatory or immune response, and/or a $GABA_B$ receptor agonist.

In certain embodiments in the various "combination" methods, compounds, kits, or formulations described above (and below herein) the GABA analogue, or GABA agonist is a $GABA_A$ receptor specific or preferential agonist. In certain embodiments in the various "combination" methods, compounds, kits, or formulations described above (and below herein) the GABA analogue, or GABA agonist is a $GABA_B$ receptor specific or preferential agonist. In certain embodiments in the various "combination" methods, compounds, kits, or formulations described above (and below herein) the GABA analogue, or GABA agonist, is one that does not substantially cross the blood-brain barrier. In certain embodiments in the various "combination" methods, compounds, kits, or formulations described above (and below herein) the first compound is GABA. In certain embodiments in the various "combination" methods, compounds, kits, or formulations described above (and below herein) the first compound is selected from the group consisting of GABA, muscimol, THIP/gaboxadol, Isoguvacine, Kojic amine, Homotaurine, Homohypotaurine, Trans-aminocyclopentane-3-carboxylic acid, Trans-amino-4-crotonic acid, β-guanidinopropionic acid, homo-β-proline, Isonipecotic acid, 3-((aminoiminomethyl)thio)-2-propenoic acid (ZAPA), Imidazoleacetic acid, and piperidine-4-sulfonic acid (P4S). In certain embodiments in the various "combination" methods, compounds, kits, or formulations described above (and below herein) the first compound is selected from the group consisting of thiopental, thiamylal, pentobarbital, secobarbital, hexobarbital, butobarbital, amobarbital, barbital, mephobarbital, phenobarbital, primidone, midazolam, triazolam, lometazepam, flutazolam, nitrazepam, fluritrazepam, nimetazepam, diazepam, medazepam, oxazolam, prazeam, tofisopam, rilmazafonoe, lorazepam, temazepam, oxazepam, fluidazepam, chlordizaepoxide, cloxazolam, flutoprazepam, alprazolam, estazolam, bromazepam, flurazepam, clorazepate potassium, haloxazolam, ethyl loflazepate, qazepam, clonazepam, mexazolam, etizolam, brotizolam, clotizaepam, propofol, and fospropofol, zolpidem, zopiclone, and exzopiclone. In certain embodiments in the various "combination" methods, compounds, kits, or formulations described above (and below herein) the first compound is not a barbituate, and/or not a benzodiazepine, and/or not a thienodiazepine, and/or not a dialkylphenol. In certain embodiments in the various "combination" methods, compounds, kits, or formulations described above (and below herein) the first compound is not GABA.

In certain embodiments in the various "combination" methods, compounds, kits, or formulations described above (and below herein) the second compound is a β-cell antigen and/or a nucleic acid encoding a β-cell antigen and/or an immune cell specific immunosuppressant. In certain embodiments in the various "combination" methods, compounds, kits, or formulations described above (and below herein) the second compound comprises one or more β-cell antigens or a nucleic acid encoding one or more of said antigens, wherein said antigens comprise an antigen selected from the group consisting of GAD (GAD65), GAD67, hsp65 or an immunogenic fragment thereof, an insulin b-chain or immunogenic fragment thereof, an HSPp277 or immunogenic fragment thereof, an MHC molecule from an islet donor cell or an immunogenic fragment thereof, pro-insulin or an immunogenic fragment thereof, preproinsulin or an immunogenic fragment thereof, islet-specific glucose 6 phosphatase catalytic subunit-related protein (IGRP) or an immunogenic fragment thereof, chromogranin A or an immunogenic fragment thereof, insulinoma antigen-2 or an immunogenic fragment thereof, and ZnT8 or an immunogenic fragment thereof. In various embodiments the antigen is combined with an adjuvant (e.g., alum). In certain embodiments in the various "combination" methods, compounds, kits, or formulations described above (and below herein) the second compound comprises a composition selected from the group consisting of an antigen that has a therapeutic effect in type I diabetes, an anti-CD3 antibody, exendin-4, and a pro-insulin therapeutic. In certain embodiments in the various "combination" methods, compounds, kits, or formulations described above (and below herein) the second compound comprises a non-activating anti-CD3 monoclonal antibody. In certain embodiments in the various "combination" methods, compounds, kits, or formulations described above (and below herein) the second compound comprises a hOKT3γ1(Ala-Ala) monoclonal antibody or an anti-CD3 F(ab')$_2$. In certain embodiments in the various "combination" methods, compounds, kits, or formulations described above (and below herein) the second compound comprises a composition selected from the group consisting of Alpha-1 Antitrypsin (AAT), Canakinumab, Diamyd, Exsulin, LCT, Lisofylline, Rituximab, Xoma 052, DiaPep277, Prochymal, Reparixin, Thymoglobulin, Ilaris (canakinumab), Januvia and Prevacid, Alpha-antitrypsin, and Amevive (alefacept). In certain embodiments in the various "combination" methods, compounds, kits, or formulations described above (and below herein) the compound comprises a factor that stimulates a regulatory and/or immune response (e.g., an interleukin-2 or an analogue thereof, TGFβ or an analogue thereof, IL-10 or an analogue thereof, an IL-6 antagonist, an IL-23 antagonist, a CD25 antagonist, an anti-IL-6 antibody, anti-IL-23 antibody, and an anti-CD25 antibody). In certain embodiments in the various "combination" methods, compounds, kits, or formulations described above (and below herein) the second compound has anti-inflammatory activity and/or is a regulator of an immune response. In certain embodiments in the various "combination" methods, compounds, kits, or formulations described above (and below herein) the second compound comprises a compound selected from the group consisting of an anti-CD3 antibody, anti-TNF, anti-IFN, CTLA-4 fused to Ig, anti-thymocyte globulin, anti-CD3 antibody (muromonab or Otelixizumab), sirolimus, and mycophenolate. In certain embodiments in the various "combination" methods, compounds, kits, or formulations described above (and below herein) the second compound comprises a compound selected from the group consisting of Azathioprine, Mycophenolic acid, Leflunomide, Teriflunomide, methotrexate, FKBP/Cyclophilin/Calcineurin, Tacrolimus, Ciclosporin, Pimecrolimus, Abetimus, Gusperimus, Thalidomide, Lenalidomide, Sirolimus, Deforolimus, Everolimus, Temsirolimus, Zotarolimus, Biolimus A9, and Anakinra. In certain embodiments in the various "combination" methods, compounds, kits, or formulations described above (and below herein) the second compound comprises a compound selected from the group consisting of anti-Complement component 5 (Eculizumab), anti-TNFs (Infliximab, Adalimumab, Certolizumab pegol, Afelimomab, Golimumab, Nerelimomab), anti-Interleukin 5 (Mepolizumab), anti-imunoglobulin E (Omalizumab), anti-Interferon (Faralimomab), anti-IL-6 (Elsilimomab), anti-IL-12 and anti-IL-23 (Lebrikizumab, Ustekinumab), anti-CD3 (Muromonab-CD3, Otelixizumab, Teplizumab, Visilizumab), anti-CD4 (Clenoliximab, Keliximab, Zanolimumab), anti-CD11a (Efalizumab), anti-CD18 (Erlizumab), anti-CD20 (Afutuzumab, Rituximab, Ocrelizumab, Pascolizumab), anti-CD23 (Lumiliximab), anti-CD40 (Teneliximab, Toralizumab), anti-CD62L/L-selectin (Aselizumab), anti-CD80 (Galiximab), anti-CD147/Basigin (Gavilimomab), anti-CD154 (Ruplizumab), anti-BLyS (Belimumab), CTLA-4 (Ipilimumab, Tremelimumab), CAT (Bertilimumab, Lerdelimumab, Metelimumab), anti-Integrin (Natalizumab), anti-Interleukin-6 receptor (Tocilizumab), anti-LFA-1 (Odulimomab), anti-IL-2 receptor/CD25 (Basiliximab, Daclizumab, Inolimomab), anti-T-lymphocyte (Zolimomab aritox), Atorolimumab, Cedelizumab, Dorlixizumab, Fontolizumab, Gantenerumab, Gomiliximab, Maslimomab, Morolimumab, Pexelizumab, Reslizumab, Rovelizumab, Siplizumab, Talizumab, Telimomab aritox, Vapaliximab, Vepalimomab, Anti-thymocyte globulin, Anti-lymphocyte globulin, CTLA-4 (Abatacept, Belatacept), TNF inhibitor (Etanercept, Pegsunercept), Aflibercept, Alefacept, and Rilonacept. In certain embodiments second compound has no agonistic activity at a GABA receptor (e.g., at a $GABA_A$ receptor and/or at a $GABA_B$ receptor, and/or at a $GABA_C$ receptor). In certain embodiments the second compound has agonistic activity at a $GABA_B$ receptor. In certain embodiments the second compound has agonistic activity at a $GABA_B$ receptor and is selected from the group consisting of baclofen, (3-amino-2(S)-hydroxypropyl)methylphosphinic acid (CGP 44532), 3-aminopropyl(methyl)phosphinic acid (SKF 97541), and 3-aminopropylphosphonic acid (3-APA), (3-amino-2-fluoropropyl)phosphinic acid; (2R)-(3-amino-2-fluoropropyl)phosphinic acid; (2S)-(3-amino-2-fluoropropyl)phosphinic acid; (3-amino-2-fluoro-1-methylpropyl)phosphinic acid; (3-amino-2-oxopropyl) phosphinic acid; (2S)-(3-amino-2-hydroxypropyl) phosphinic acid; (R)-(3-amino-2-hydroxypropyl)phosphinic acid; and (3-amino-1-fluoro-2-hydroxypropyl)phosphinic acid. Illustrative species of Formula III include (3-amino-2-fluoropropyl)sulphinic acid, (2S)-(3-amino-2-fluoropropyl)sulphinic acid, (2R)-(3-amino-2-fluoropropyl)sulphinic acid, (2S)-(3-amino-2-hydroxypropyl)sulphinic acid, and (2R)-(3-amino-2-hydroxypropyl)sulphinic acid and (3-amino-2-oxopropyl)sulphinic acid. In certain embodiments in the various "combination" methods, compounds, kits, or formulations described above (and below herein) the first compound is administered before said second compound; or first compound is administered after said second compound. In certain embodiments in the various "combination" methods, compounds, kits, or formulations described above (and below herein) the first compound is administered simultaneously with said second compound (e.g., the first compound and the second compound can be combined in a single formulation or simply administered essentially simultaneously). In certain embodiments in the various "combination" methods, compounds, kits, or formulations described above (and below herein) the combination of the first compound and the second compound is synergistic. In certain embodiments in the various "combination" methods, compounds, kits, or formulations described above (and below herein) the mammal is a human. In certain embodiments in the various "combination" methods, compounds, kits, or formulations described above (and below herein) the mammal (e.g., human) is diagnosed as having type I diabetes or determined to be at risk for type I diabetes. In certain embodiments in the various "combination" methods, compounds, kits, or formulations described above (and below herein) the mammal (e.g., human) is diagnosed as having hyperglycemia or being at risk for hyperglycemia. In certain embodiments in the various "combination" methods, compounds, kits, or formulations described above (and below herein) the mammal (e.g., human) contains transplanted islet cells. In certain embodiments in the various "combination" methods, compounds, kits, or formulations described above (and below herein) the mammal is not a mammal diagnosed as having or at risk for one or more conditions selected from the group consisting of a sleep disorder or insomnia, CNS disorder (e.g., muscle relaxation in spinal spasticity) a cardiovascular disorders, asthma, a gut motility disorder (e.g., irritable bowel syndrome), a subject being treated with a prokinetic and/or anti-tussive agents, a subject treated for emesis, a subject diagnosed as having or at risk for an autoimmune disease (e.g., rheumatoid arthritis), a subject diagnosed as having or at risk for a neurophysiological or neurophsychiatric disorder, a subject as having or at risk for a psychiatric disorder (e.g., anxiety and/or depression) a subject diagnosed as having or at risk for Huntington's disease and/or Parkinson's disease, and/or a subject having or at risk for MS.

Definitions

A "receptor agonist" as used herein refers to the native ligand of that receptor (e.g., a GABA receptor) to analogues thereof or other ligands that similarly "activate" the receptor, and/or to a positive allosteric modulator of the receptor.

A "$GABA_A$ receptor specific agonist" refers to an agent that has agonistic activity at the $GABA_A$ receptor and substantially no agonist activity at the $GABA_B$ and/or $GABA_C$ receptor. A "$GABA_A$ receptor preferential agonist" refers to an agent that has greater agonistic activity at the $GABA_A$ receptor than at the $GABA_B$ and/or $GABA_C$ receptor. In certain embodiments the $GABAB_A$ receptor preferential agonist has at least 1.2-fold, more preferably at least 1.5 fold still more preferably at least 2 fold, and most preferably at least 3-fold, at least 5-fold, or at least 10-fold greater activity at the $GABA_A$ receptor than at the $GABA_B$ and/or $GABA_C$ receptor as determined using an conventional assay for agonist activity at a GABA receptor.

A "$GABA_B$ receptor specific agonist" refers to an agent that has agonistic activity at the $GABA_B$ receptor and substantially no agonist activity at the $GABA_A$ and/or $GABA_C$ receptors. A "$GABA_B$ receptor preferential agonist" refers to an agent that has greater agonistic activity at the $GABA_B$ receptor than at the $GABA_A$ and/or $GABA_C$ receptors. In certain embodiments the $GABAB_B$ receptor preferential agonist has at least 1.2-fold, more preferably at least 1.5 fold still more preferably at least 2 fold, and most preferably at least 3-fold, at least 5-fold, or at least 10-fold greater activity at the $GABA_B$ receptor than at the $GABA_A$ and/or $GABA_C$ receptors as determined using an conventional assay for agonist activity at a GABA receptor.

As used herein, "administering" refers to local and systemic administration, e.g., including enteral, parenteral, pulmonary, and topical/transdermal administration. Routes of administration for compounds (e.g., GABA, GABA agonists, β-cell autoantigens, immunomodulators, anti-inflammatories, etc.) that find use in the methods described herein include, e.g., oral (per os (po)) administration, nasal or inhalation administration, administration as a suppository, topical contact, transdermal delivery (e.g., via a transdermal patch), intrathecal (IT) administration, intravenous ("iv") administration, intraperitoneal ("ip") administration, intramuscular ("im") administration, intralesional administration, or subcutaneous ("sc") administration, or the implantation of a slow-release device e.g., a mini-osmotic pump, a depot formulation, etc., to a subject. Administration can be by any route including parenteral and transmucosal (e.g., oral, nasal, vaginal, rectal, or transdermal). Parenteral administration includes, e.g., intravenous, intramuscular, intra-arterial, intradermal, subcutaneous, intraperitoneal, intraventricular, ionophoretic and intracranial. Other modes of delivery include, but are not limited to, the use of liposomal formulations, intravenous infusion, transdermal patches, etc.

The terms "systemic administration" and "systemically administered" refer to a method of administering a compound or composition to a mammal so that the compound or composition is delivered to sites in the body, including the targeted site of pharmaceutical action, via the circulatory system. Systemic administration includes, but is not limited to, oral, intranasal, rectal and parenteral (e.g., other than through the alimentary tract, such as intramuscular, intravenous, intra-arterial, transdermal and subcutaneous) administration.

The phrase "cause to be administered" refers to the actions taken by a medical professional (e.g., a physician), or a person controlling medical care of a subject, that control and/or permit the administration of the agent(s)/compound(s) at issue to the subject. Causing to be administered can involve diagnosis and/or determination of an appropriate therapeutic or prophylactic regimen, and/or prescribing particular agent(s)/compounds for a subject. Such prescribing can include, for example, drafting a prescription form, annotating a medical record, and the like.

As used herein, the terms "treating" and "treatment" refer to delaying the onset of, retarding or reversing the progress of, reducing the severity of, or alleviating or preventing either the disease or condition to which the term applies, or one or more symptoms of such disease or condition.

The term "mitigating" refers to reduction or elimination of one or more symptoms of that pathology or disease, and/or a reduction in the rate or delay of onset or severity of one or more symptoms of that pathology or disease, and/or the prevention of that pathology or disease. In certain embodiments, the reduction or elimination of one or more symptoms of pathology or disease can include, but is not limited to, reduction or elimination of one or more markers that are characteristic of the pathology or and/or reduction, stabilization or reversal of one or more diagnostic criteria.

As used herein, the phrase "consisting essentially of" refers to the genera or species of active pharmaceutical agents recited in a method or composition, and further can include other agents that, on their own do not alter or preferably do not diminish substantial activity for the recited indication or purpose. In some embodiments, the phrase "consisting essentially of" expressly excludes the inclusion of one or more additional agents that have the same or similar activity as the recited compounds.

The terms "subject," "individual," and "patient" interchangeably refer to a mammal, preferably a human or a non-human primate, but also domesticated mammals (e.g., canine or feline), laboratory mammals (e.g., mouse, rat, rabbit, hamster, guinea pig) and agricultural mammals (e.g., equine, bovine, porcine, ovine). In various embodiments, the subject can be a human (e.g., adult male, adult female, adolescent male, adolescent female, male child, female child) under the care of a physician or other health worker in a hospital, as an outpatient, or other clinical context. In certain embodiments the subject may not be under the care or prescription of a physician or other health worker.

An "immunogenic fragment" of a peptide refers to a peptide fragment that, when administered to a mammal induces an immune response. Immunogenic fragments are typically longer than 10 amino acids in length, preferably longer than about 15 or about 20 amino acids in length.

The terms "coadministration" or "administration in conjunction with" or "cotreatment" when used in reference to the coadministration of a first compound (e.g., GABA or a GABA agonist) and a second compound (e.g., GAD, and other second compounds described herein) indicates that the first compound and the second compound are administered so that there is at least some chronological overlap in the biological activity of first compound and the second compound in the organism to which they are administered. Coadministration can simultaneous administration or sequential administration. In sequential administration there may even be some substantial delay (e.g., minutes or even hours) between administration of the first compound and the second compound as long as their biological activities overlap. In certain embodiments the coadminstration is over a time frame that permits the first compound and second compound to produce an enhanced effect (e.g., therapeutic or prophylactic effect) on the organism. In certain embodiments the enhanced effect is a synergistic effect.

As used herein, an "antibody" (e.g., an anti-CD3 antibody) refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H$1 by a disulfide bond. The F(ab)'$_2$ may be reduced under mild conditions to break the disulfide linkage in the hinge region thereby converting the (Fab')$_2$ dimer into a Fab' monomer. The Fab' monomer is essentially a Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker. Huston, et al. (1988) *Proc. Nat. Acad. Sci. USA*, 85: 5879-5883. While the $V_H$ and $V_L$ are connected to each as a single polypeptide chain, the $V_H$ and $V_L$ domains associate non-covalently. The first functional antibody molecules to be expressed on the surface of filamentous phage were single-chain Fv's (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to, e.g., g3p (see, e.g., U.S. Pat. No. 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778). Particularly preferred antibodies should include all that have been displayed on phage (e.g., scFv, Fv, Fab and disulfide linked Fv (Reiter et al. (1995) *Protein Eng.* 8: 1323-1331).

As used herein, the terms "antibody" and "antibodies" include polyclonal antibodies, monoclonal antibodies, multispecific antibodies, human antibodies, humanized antibodies (fully or partially humanized), animal antibodies (e.g., derived from a mammal, including a non-primate (for example, a cow, pig, camel, llama, horse, goat, rabbit, sheep, hamsters, guinea pig, cat, dog, rat, mouse), a non-human primate (for example, a monkey, such as a cynomolgus monkey, a chimpanzee, etc.), recombinant antibodies, chimeric antibodies, single-chain Fvs (scFv), single chain antibodies, single domain antibodies, Fab fragments, F(ab')$_2$ fragments, disulfide-linked Fv (sdFv), chemically conjugated Fv (ccFv), and anti-idiotypic (anti-Id) antibodies (including, for example, anti-Id antibodies to antibodies of the present invention), and functionally active epitope-binding fragments of any of the above. In certain embodiments antibodies also include affibodies, nanobodies, and unibodies. In certain embodiments particular, antibodies include immunoglobulin molecules and immunologically active fragments of immunoglobulin molecules, namely, molecules that contain an antigen binding site. Immunoglobulin molecules can be of any type (for example, IgG, IgE, IgM, IgD, IgA and IgY), class (for example, IgG$_1$, IgG$_2$, IgG$_3$, IgG$_4$, IgA$_1$ and IgA$_2$) or subclass.

BRIEF DESCRIPTION OF THE DRAWINGS

FIG. 8A: No treatment. FIG. 8B: Mice inoculated with GAD. FIG. 8C: Mice administered GABA. FIG. 8D: Mice administered GABA and GAD.

FIG. 10A shows that GABA (both 2 mg/ml and 6 mgs/ml) and baclofen in water significantly inhibits the STZ mediated oxidative-stress-induced apoptosis. 10B shows the number of insulin-expressing cells per 100 islet cells. FIG. 10C shows the relative area of insulin+ cells to the total area of the islets. FIG. 10D shows the intensity of islet insulin staining

DETAILED DESCRIPTION

Figure 1:
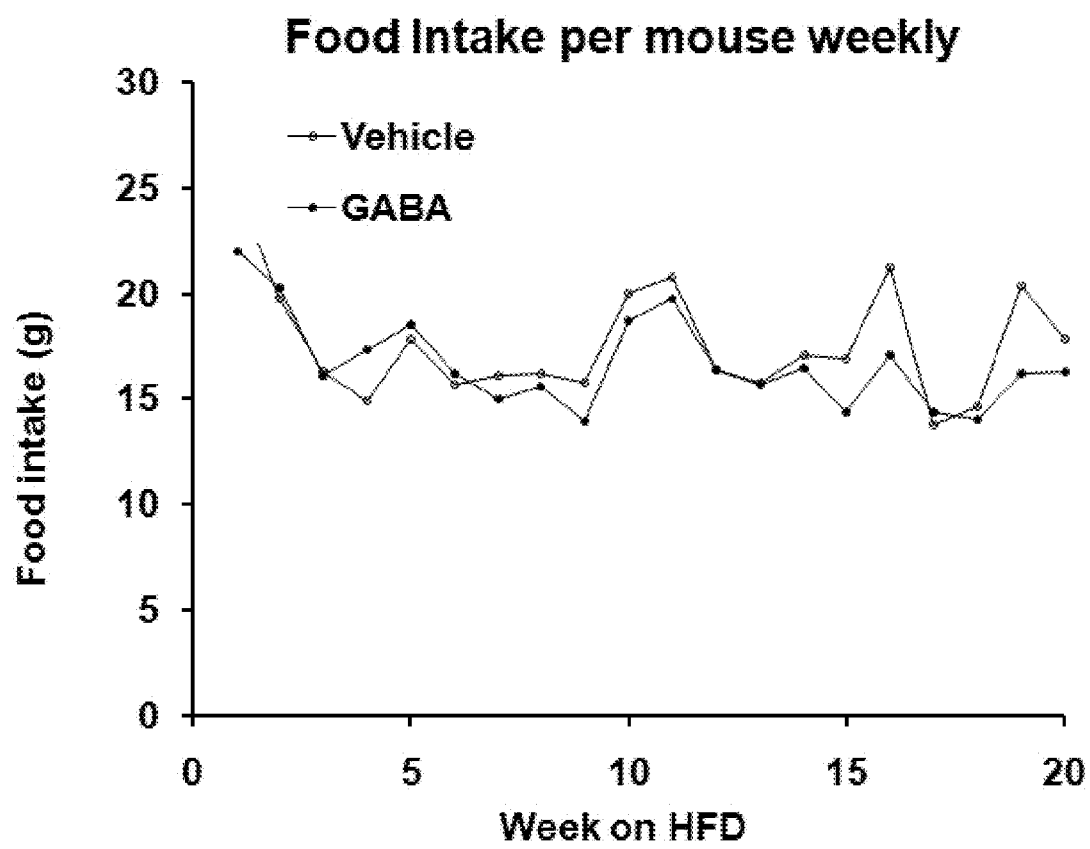
FIG. 1 illustrates the effect of GABA on food intake on HFD-fed mice.

In certain embodiments, novel methods for the treatment and prophylaxis of metabolic syndrome are provided. In particular, in certain embodiments, the use of GABA, a GABA analogue, a GABA receptor agonist, and/or a GABA prodrug, and/or a GABA receptor agonist prodrug, and/or a GABA receptor potentiator is contemplated to mitigate one or more symptoms or pathologies of metabolic syndrome or in the prophylaxis of such symptoms or pathologies.

In certain embodiments, novel methods for the treatment and/or prophylaxis of type I diabetes are provided. In particular, in certain embodiments, combinations of GABA and/or GABA agonists with other agents (e.g., compounds/compositions/agents comprising a non-GABA therapeutic agent for the treatment of type I diabetes, and/or an anti-inflammatory compound, and/or a factor that stimulates a regulatory or immune response, and/or a $GABA_B$ receptor agonist) for the treatment and/or prophylaxis of type I diabetes. In certain embodiments these multi-component methods can be used to ameliorate one or more symptoms or disorders associated with metabolic syndrome, and/or delay the onset of type I diabetes, and/or slow the progression of type I diabetes, and/or reduce the severity of type I diabetes, and/or reverse type I diabetes in a mammal; and/or to promote transplanted islet cell survival in a mammal; and/or to delay the onset of hyperglycemia, and/or to slow the progression of hyperglycemia, and/or to reduce the severity of hyperglycemia, and/or to reverse hyperglycemia in a mammal; and/or to promote transplanted islet cell survival in a mammal having type I diabetes or at risk for type I diabetes who is a recipient of transplanted islet cells; and/or to delay the onset of an immune response, and/or slow the progression of an immune response, and/or reduce the severity of an immune response, and/or suppress an immune response in a mammal; and/or to protect beta-cells in a mammal from oxidative stress induced apoptosis Treatment and/or Prophylaxis of Metabolic Syndrome (e.g. Type II Diabetes).

Metabolic syndrome is a group of risk factors characterized by impaired glucose tolerance, reduced insulin sensitivity, hypertension, hyperlipidemia, obesity and chronic inflammation. Inflammation is thought to be involved since a number of inflammatory molecules as IL-6, TNFα and C-reactive protein are increased. Individuals with metabolic disease have higher risk for cardiovascular diseases, heart attack, stroke, type 2 diabetes (T2D) and nonalcoholic liver disease.

It was shown that $GABA_A$ receptors are expressed by T cells and that administration of GABA inhibits the development of the autoimmune disease Type 1 diabetes and delay type I hypersensitivity in mice. Data illustrated herein (see, e.g., Example 1) relate to GABA's ability to downregulate inflammation in a non-autoimmune context. It is shown that including GABA in the diet of mice that are developing obesity reduces their insulin resistance, improves their glucose tolerance, reduces immune (e.g., macrophage) infiltrates into their adipose tissue, reduces the mass of adipocytes, and reduces obesity. Accordingly, GABA treatment has relevance for ameliorating risk factors of metabolic syndrome, cardiovascular disease and T2D. Without being bound to a particular theory, it is believed the mechanisms may involve (but are not limited to); 1) GABA binding to $GABA_A$-receptors on immune cells and limiting their inflammatory responses, or promoting their anti-inflammatory responses, and/or 2) GABA binding to $GABA_B$-receptors on β-cells and promoting their health or replication, and/or 3) GABA binding to GABA receptors on adipose cells and thereby modulating glucose and lipid metabolism.

It was demonstrated that in mice fed a "western diet" causing which typically causes weight gain, obesity, glucose intolerance, insulin resistance and metabolic syndrome, the administration of GABA improved glucose tolerance, improved insulin sensitivity (i.e., reduced insulin intolerance), reduced fasting blood glucose levels, mitigated the HFD-induced obesity (body weight), inhibited the infiltration of macrophages into white adipose tissue, and significantly reduced the mass of adipocytes.

Thus, even though the two groups of mice had similar food and water consumption, there were very important differences between the groups in terms of their glucose tolerance, insulin sensitivity, inflammation in fatty tissue and obesity.

Accordingly it is believed that the administration of GABA, other GABA receptor agonists or partial agonists, or drugs that modulate GABA-receptor expression or time on the cell surface are excellent agent useful for treatment or prophylaxis of metabolic syndrome and the associated hypertension, cardiovascular disease, insulin resistance-related obesity, T2D, nonalcoholic liver disease and other diseases.

Accordingly, in certain embodiments, methods for the treatment and/or prophylaxis of one or more symptoms and/or conditions associated with metabolic disease are contemplated. In various embodiments the methods involve administering to a subject in need thereof, a GABA, and/or a GABA analogue (e.g., a GABA receptor agonist/ligand), a GABA receptor agonist prodrug, and/or a GABA potentiator (e.g., a $GABA_A$ receptor potentiator) in a therapeutically or prophylactically effective amount. In certain embodiments the GABA In certain embodiments the GABA agonist is a $GABA_A$ receptor specific or $GABA_A$ receptor preferential agonist. These methods provide therapy or prophylaxis for insulin resistance, and/or glucose intolerance, and/or hypertension, and/or fatty liver disease, and/or to reduce macrophage infiltration into adipose tissue, and/or mitigate chronic kidney disease, and/or obesity.

In certain embodiments, a method of slowing or stopping the progression from a pre-diabetic condition in a mammal or from a non-diabetic condition in a mammal at risk for type II diabetes to type II diabetes is provided. In certain embodiments the method involves administering to a subject in need thereof, a GABA, and/or a GABA analogue (e.g., a $GABA_A$ receptor agonist/ligand), a GABA or GABA receptor agonist prodrug, and/or a GABA potentiator (e.g., a $GABA_A$ receptor potentiator) in an amount sufficient to slow or stop the progression from a pre-diabetic condition or from a non-diabetic condition to type II diabetes.

Combination Therapies for the Treatment and/or Prophylaxis of Type I Diabetes.

The combination of GABA with other therapeutic or potentially therapeutic moieties for efficacy in diabetes, especially type I diabetes and related pathologies was also examined (see, e.g., Examples 2-4).

In one embodiment, the use of a vaccine comprising a GAD vaccine with GABA was investigated and it was determined that the combination therapy has synergistic effects. Accordingly it is believed that lower dosages of each component can be effective when used in combination than as monotherapies and/or that elevated efficacy can be obtained with the combined administration than either component alone. Accordingly, in certain embodiments, a method of treatment and/or prophylaxis of type I diabetes is provided. In certain embodiments a method of delaying the onset of type I diabetes, and/or slowing the progression of type I diabetes, and/or reducing the severity of type I diabetes, and/or reversing type I diabetes in a mammal is provided. The method typically involves coadministering to the mammal a first compound or composition comprising GABA, and/or a GABA analogue (e.g., a GABA receptor agonist/ligand), a GABA prodrug or GABA receptor agonist prodrug, and/or a GABA potentiator (e.g., a $GABA_A$ receptor potentiator) and a second compound or composition comprising a non-GABA therapeutic agent for the treatment of type I diabetes, and/or an anti-inflammatory compound, and/or a factor that stimulates a regulatory or immune response, and/or a $GABA_B$ receptor agonist. In certain embodiments the second compound or composition comprises a non-GABA therapeutic agent for the treatment of type I diabetes where the first compound or composition and the second compound or composition are administered in an amount sufficient to delay the onset of type I diabetes, and/or slow the progression of type I diabetes, and/or reduce the severity of type I diabetes, and/or reverse type I diabetes in said mammal. In certain embodiments the non-therapeutic agent for the treatment of type I diabetes comprises an immune-cell specific or immune cell preferential immunosuppressant and/or a method a β-cell antigen and/or a nucleic acid encoding a β-cell antigen (e.g., as described herein).

Using an islet transplantation model it was demonstrated that both GABA and GAD vaccination monotherapies have a beneficial effect towards protecting syngenic islet grafts in diabetic NOD mice. In particular, it was demonstrated that GAD/adjuvant (e.g. GAD/alum) and GABA monotherapies each can prolong syngenic islet graft survival for a few weeks in diabetic NOD mice. But together, GABA+GAD/alum treatment has a clear synergistic long-term beneficial effect. The long-term protection of syngenic islets in diabetic NOD mice is somewhat remarkable since this is without any strong immunosuppressants. Moreover, the efficacy of GABA+GAD/alum treatment is very promising even when compared to previously published combination therapy using the islet transplantation model Accordingly, in certain embodiments, a method of promoting transplanted islet cell survival in a mammal having Type I diabetes or at risk for type I who is a recipient of transplanted islet cells, said method comprising. The method typically involves coadministering to the mammal a first compound or composition comprising GABA, and/or a GABA analogue (e.g., a GABA receptor agonist/ligand), a GABA prodrug or GABA receptor agonist prodrug, and/or a GABA potentiator (e.g., a $GABA_A$ receptor potentiator) and a second compound or composition comprising a non-GABA therapeutic agent for the treatment of type I diabetes (e.g., a β-cell antigen or a nucleic acid encoding a β-cell antigen). The first compound or composition and the second compound or composition are administered in an amount sufficient to promoting transplanted islet cell survival in the mammal. In certain embodiments the non-therapeutic agent for the treatment of type I diabetes comprises an immune-cell specific or immune cell preferential immunosuppressant and/or a method a β-cell antigen and/or a nucleic acid encoding a β-cell antigen (e.g., as described herein).

It was also demonstrated that GAD+GABA has synergistic effects and can reverse hyperglycemia in newly diabetic mice. While it is generally believed that no antigen-based therapy can reverse hyperglycemia in newly diabetic NOD mice, we show that GABA+GAD (e.g. GAD/alum) has a synergistic effect and can efficiently reverse T1D in NOD mice. Again, the efficacy of GABA+GAD/alum treatment is impressive. Accordingly, in certain embodiments, a method of treatment and/or prophylaxis of hyperglycemia (e.g., hyperglycemia associated with a pre-diabetic or present type I diabetic condition) is provided. In certain embodiments a method of delaying the onset of hyperglycemia, and/or slowing the progression of hyperglycemia, and/or reducing the severity of hyperglycemia, and/or reversing hyperglycemia in a mammal is provided. The method typically involves coadministering to the mammal a first compound or composition comprising GABA, and/or a GABA analogue (e.g., a GABA receptor agonist/ligand), a GABA prodrug or GABA receptor agonist prodrug, and/or a GABA potentiator (e.g., a $GABA_A$ receptor potentiator) and a second compound or composition comprising a non-GABA therapeutic agent for the treatment of type I diabetes, and/or an anti-inflammatory compound, and/or a factor that stimulates a regulatory or immune response, and/or a $GABA_B$ receptor agonist. In certain embodiments the second compound or composition comprises a non-GABA therapeutic agent for the treatment of type I diabetes. The first compound or composition and the second compound or composition are administered in an amount sufficient to delay the onset of hyperglycemia, and/or slow the progression of hyperglycemia, and/or reduce the severity of hyperglycemia, and/or reverse hyperglycemia in the mammal. In certain embodiments the non-therapeutic agent for the treatment of type I diabetes comprises an immune-cell specific or immune cell preferential immunosuppressant and/or a method a β-cell antigen and/or a nucleic acid encoding a β-cell antigen (e.g., as described herein).

Additionally, it was demonstrated that GABA and baclofen (a GABA-B receptor agonist) treatment can protect β-cells from oxidative stress induced apoptosis. We show that data below as well. Accordingly, in certain embodiments, method of protecting beta-cells from oxidative stress induced apoptosis, said method comprising administering to a mammal containing said β-cells is provided. The method typically involves coadministering to the mammal a first compound or composition comprising GABA, and/or a GABA analogue (e.g., a GABA receptor agonist/ligand), a GABA prodrug or GABA receptor agonist prodrug, and/or a GABA potentiator (e.g., a $GABA_A$ receptor potentiator) and a second compound or composition comprising a non-GABA therapeutic agent for the treatment of type I diabetes, and/or an anti-inflammatory compound, and/or a factor that stimulates a regulatory or immune response, and/or a $GABA_B$ receptor agonist. In certain embodiments the second compound or composition comprises a compound having agonistic activity at a $GABA_B$ receptor (e.g., baclofen). The first compound or composition and the second compound or composition are administered in an amount sufficient to partially or fully protect beta-cells from oxidative stress induced apoptosis in the mammal.

The combination of GABA and GABA agonists and immune system modulators was also examined. It was determined that such combinations can also be used for the treatment or prophylaxis of hyperglycemia (e.g., hyperglycemia associated with a pre-diabetic or present type I diabetic condition) is provided. In certain embodiments a method of delaying the onset of hyperglycemia, and/or slowing the progression of hyperglycemia, and/or reducing the severity of hyperglycemia, and/or reversing hyperglycemia in a mammal is provided. The method typically involves coadministering to the mammal a first compound or composition comprising GABA, and/or a GABA analogue (e.g., a GABA receptor agonist/ligand), a GABA prodrug or GABA receptor agonist prodrug, and/or a GABA potentiator (e.g., a $GABA_A$ receptor potentiators) and a second compound or composition comprising a non-GABA therapeutic agent for the treatment of type I diabetes, and/or an anti-inflammatory compound, and/or a factor that stimulates a regulatory or immune response, and/or a $GABA_B$ receptor agonist. In certain embodiments the second compound or composition comprises a factor that stimulates a regulatory and/or immune response (e.g. an interleukin-2 or an analogue thereof, TGFβ or an analogue thereof, IL-10 or an analogue thereof, an IL-6 antagonist, an IL-23 antagonist, a CD25 antagonist, an anti-IL-6 antibody, anti-IL-23 antibody, and an anti-CD25 antibody, and the like).

In certain embodiments a method of delaying the onset of an immune response, and/or slowing the progression of an immune response, and/or reducing the severity of an immune response, and/or suppressing an immune response in a mammal is provided. The method typically involves coadministering to the mammal a first compound or composition comprising GABA, and/or a GABA analogue (e.g., a GABA receptor agonist/ligand), a GABA prodrug or GABA receptor agonist prodrug, and/or a GABA potentiator (e.g., a $GABA_A$ receptor potentiator) and a first compound comprising GABA, a GABA analogue, a GABA agonist, a GABA or GABA agonist prodrug, and/or a GABA potentiator; and a second compound or composition comprising a non-GABA therapeutic agent for the treatment of type I diabetes, and/or an anti-inflammatory compound, and/or a factor that stimulates a regulatory or immune response, and/or a $GABA_B$ receptor agonist. In certain embodiments the second compound or composition has anti-inflammatory activity (e.g., an anti-CD3 antibody, anti-TNF, anti-IFN, CTLA-4 fused to Ig, anti-thymocyte globulin, anti-CD3 antibody (muromonab or Otelixizumab), sirolimus, and mycophenolate).

It is noted that the GABA treatment can both suppress autoimmune responses by working on GABA-A receptors on immune cells, and promote β-cell survival through their GABA-B receptors. We also have preliminary data that GABA can promote Treg responses (using IL-2 and anti-CD3 in an in vitro culture system).

In view of these data, it is believed that GABA-based (e.g., GABA receptor agonist based) therapies have excellent potential for translation to the clinic. GABA treatment is not limited to combination with GAD/alum-it can also be combined with proinsulin-based therapies, anti-CD3, exendin-4, or other therapeutic candidates. Because of the multiple beneficial effects of GABA treatment and its safety in humans combined GABA therapeutics are of great interest.

In this context, it is noted that pharmaceutical companies have put extensive efforts into developing GABA-receptor ligands that pass through the blood brain barrier to modulate GABA receptors on CNS neurons and have ignored the ligands that do not pass through the blood brain barrier. Without being bound to a particular theory, it is believed that such drugs that stay in the periphery are excellent for modulating immune cell and β-cell GABA-receptors (e.g., in the methods described herein) without incurring CNS effects.

It is noted that in various embodiments, the combined agents described herein produce synergistic activity.

GABA and GABA Receptor Agonists, Potentiators, and Prodrugs.

In various embodiments the methods described herein involve administering to a mammal (e.g., a human diagnosed as having or at risk for one or more of the pathologies described herein) GABA, and/or a GABA analogue, and/or a GABA receptor agonist (or partial agonist), and/or a GABA potentiator, and/or a GABA prodrug. In certain embodiments the GABA receptor agonist acts at both $GABA_A$ and $GABA_B$ receptors. In certain embodiments the GABA receptor agonist acts preferentially, or exclusively, at the $GABA_A$ or $GABA_B$ receptor.

GABA receptor agonists are well known to those of skill in the art. Illustrative GABA receptor agonists include, but are not limited to, certain barbituates (e.g., thiopental, thiamylal, pentobarbital, secobarbital, hexobarbital, butobarbital, amobarbital, barbital, mephobarbital, phenobarbital, primidone, and the like), certain benzodiazepines (e.g., midazolam, triazolam, lometazepam, flutazolam, nitrazepam, fluritrazepam, nimetazepam, diazepam, medazepam, oxazolam, prazeam, tofisopam, rilmazafonoe, lorazepam, temazepam, oxazepam, fluidazepam, chlordizaepoxide, cloxazolam, flutoprazepam, alprazolam, estazolam, bromazepam, flurazepam, clorazepate potassium, haloxazolam, ethyl loflazepate, qazepam, clonazepam, mexazolam, and the like), certain thienodiazepiens (e.g., etizolam, brotizolam, clotizaepam, and the like), certain dialkylphenols (e.g., propofol, fospropofol, and the like), certain non-benzodiazepines (e.g., zolpidem, zopiclone, exzopiclone, etc.), and the like.

GABA and certain GABA agonists penetrate the blood brain barrier (see, e.g., Table 1), while others do not. It is believed that either can be used in the methods described herein.

TABLE 1

Illustrative $GABA_A$ receptor agonists that cross BBB.

| Chemical compound | Chemical name | CAS-Registry No. | Synthesis | Structure |
|---|---|---|---|---|
| Muscimol | 5-(aminomethyl)-isoxazol-3-ol | 2763-96-4 | Chiarino et al. (1986) *Tetrahedron Letts*, 27: 3181-3182 (1986); Krogsgaard-Larsen. and Christensen (1976) *Actu Chem. Scond.* B30, 281-282. | 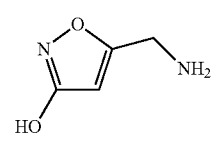 |
| THIP/ gaboxadol | 4,5,6,7-tetrahydro-[1,2]oxazolo[5,4-c]pyridin-3-one | 64603-91-4 | US Patent App. No: 2007/0203216 A1; EP Patent No. 0000338; Krosgsgaard-Larsen. (1977) *Actu Chem. Seond.* B31, 584-588. | 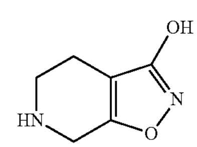 |

TABLE 1-continued

Illustrative GABA_A receptor agonists that cross BBB.

| Chemical compound | Chemical name | CAS-Registry No. | Synthesis | Structure |
|---|---|---|---|---|
| Isoguvacine | 1,2,3,6-tetrahydropyridine-4-carboxylic acid | 64603-90-3 | Krogsgaard-Larsen et al. (1978) *Neurochem.* 30: 1377 | 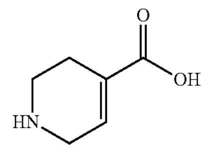 |
| Kojic amine | 2-(aminomethyl)-5-hydroxypyran-4-one | 68642-64-8 | Atkinson, et al. (1979), *J. Med. Chem.* 22 (1): 99-106 | Kojic amine |

However, without being bound to a particular theory, it is believed the methods described herein exploit the activity of GABA agonists on cells and tissues other than the brain. Accordingly, the ability to cross the blood brain barrier is not required, and may be less preferred. For example, by using compounds that do not cross the blood brain barrier numerous neurologic side effects can be avoided. Thus, in certain preferred embodiments, GABA and certain GABA agonists that don't cross the blood brain barrier (see, e.g., Table 2) are contemplated.

TABLE 2

Illustrative GABA_A receptor agonists that don't efficiently get through the BBB.

| Chemical compound | Chemical name | CAS-Registry No. | Synthesis | Structure |
|---|---|---|---|---|
| GABA | 4-aminobutanoic acid | 56-12-2 | Buddhala et al. (2009) *Neurochem. Int.* 55(1-3): 9-12. | 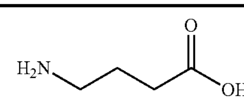 |
| Homotaurine | 3-Aminopropane-1-sulfonic acid | 3687-18-1 | Sen (1962) *Canadian J. Chem.*, 40: 2189-2191. | 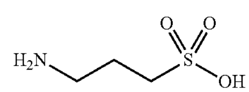 |
| Homohypotaurine | 3-aminopropane-1-sulfinic acid | 25346-09-2 | De Marco and Rinaldi (1973) *Analyt. Biochem.* 51: 65-276. | 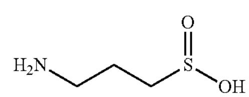 |
| Trans-aminocyclopentane-3-carboxylic acid | Same | 57376-72-4 | Sambre et al. (985), *Int. J. Appl. Radiation and Isotopes*, 36(4): 275-278. | 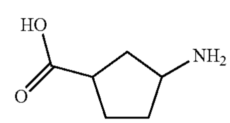 |
| Trans-amino-4-crotonic acid | (E)-4-aminobut-2-enoic acid | 25747-40-4 | Johnston et al. (1975) *J. Neurochem.* 24: 157-160 | 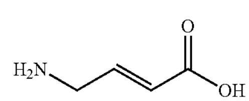 |
| β-guanidinopropionic acid | 3-(diaminomethylideneamino)propanoic acid | 353-06-3 | | 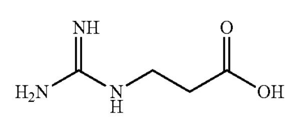 |
| homo-β-proline | 2-pyrrolidin-2-ylacetic acid | 56879-46-0 | Nielson et al. (1990) *J. Med. Chem.*, 33(1): 71-77. | 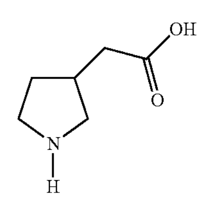 |

TABLE 2-continued

Illustrative GABA$_A$ receptor agonists that don't efficiently get through the BBB.

| Chemical compound | Chemical name | CAS-Registry No. | Synthesis | Structure |
|---|---|---|---|---|
| Isonipecotic acid | piperidine-4-carboxylic acid | 0 | Osadchenko and Tomilov (2006) *Russian J. Applied Chem.* 79(3): 499-500. | 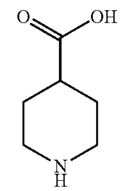 |
| 3-((aminoiminomethyl)thio)-2-propenoic acid (ZAPA) | (Z)-3-carbamimidoyl sulfanylprop-2-enoic acid | 92138-10-8 | | 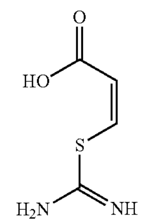 |

TABLE 3

Other GABA receptor agonists

| Chemical compound | Chemical name | CAS-Registry No. | Synthesis | Structure |
|---|---|---|---|---|
| Imidazoleacetic acid | 2-(1H-imidazol-5-yl)acetic acid | 30581-89-6 | Mehler et al. (1952), *J. Bio. Chem.* 197: 475-480. | 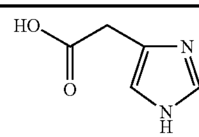 |
| Piperidine-4-sulfonic acid (P4S) | Same | 72450-62-5 | Krogsgaard et al. (1980) *J. Neurochem.* 34(3): 756-759. | 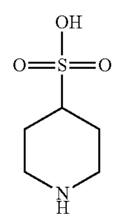 |

In addition to GABA or GABA analogues, the use of GABA$_A$ and/or GABA$_B$ receptor potentiators (e.g., positive allosteric regulators of GABA) is contemplated. In certain embodiments the potentiators bind to sites other than the GABA or GABA analogue binding site, but have GABA effects. Numerous compounds that potentiate the effects of GABA have been identified. Such compounds typically bind predominantly to sites other than the GABA binding site, such as, for example, the benzodiazepine site, the barbiturate or the steroid binding site. Such potentiators include, but are not limited to, triazolo-pyridazine derivatives (see, e.g. WO 99/37649, WO 99/37648, and WO 99/37644), pyrazolo-pyridine derivatives (see, e.g. WO 99/48892), nicotinic carboxamide compounds (see, e.g., WO 99/43661 and U.S. Pat. No. 5,723,462), neuroactive steroids (see, e.g. WO 98/05337) such as, e.g., androstane derivatives and pregnane derivatives (see, e.g., U.S. Pat. No. 5,925,630), triazolo-phthalazine derivatives (see, e.g. WO 99/25353, and WO/98/04560), tricyclic pyrazolo-pyridazinone analogues (see, e.g. WO 99/00391), and fenamates (U.S. Pat. No. 5,637,617), anxiolytic benzodiazepine, and/or pentobarbital.

Other GABA analogs (agonists) include, but are not limited to the following:

Peptide prodrug derivatives of gabapentin and other GABA analog drugs are contemplated by Bryans et al (see, e.g., PCT Publication No: WO 01/90052; U.K. Application GB 2,362,646; European Application EP 1,178,034, and the like). These applications disclose gabapentin derivatives where the amino group is blocked with particular α-aminoacyl or dipeptide moieties. More specifically, the α-amino acids comprising these peptide prodrug derivatives include the 20 naturally encoded α-amino acids, plus phenylglycine.

Prodrug derivatives of gabapentin and other GABA analog drugs are also disclosed by Gallop et al (International Applications WO 02/28881, WO 02/28883, WO 02/28411 and WO 02/32376). The compounds disclosed therein include bile acid conjugates of GABA analogs that are designed to be actively transported across the intestinal mucosa via interaction with the ileal bile acid transporter. These conjugates are further designed to undergo enterohepatic recirculation and to slowly release the parent GABA analog into the systemic circulation. Additional prodrug derivatives of gabapentin and other GABA analog drugs are disclosed by Gallop et al (see e.g., PCT Publication WO 02/42414). Compounds disclosed therein include α-aminoacyl and β-aminoacyl conjugates of GABA analogs that are designed to be actively absorbed across the intestinal mucosa via interaction with peptide transporters expressed in the intestine.

Also contemplated for use in the methods described herein are GABA analogs formulated for oral administration as described in U.S. Patent Publication No: 2008/0226716, incorporated herein by reference) where prodrugs of GABA analogs, and compositions of prodrugs of GABA analogs and methods for making prodrugs of GABA analogs are provided. The prodrugs include substrates for peptide transporters (PEPT1 and/or PEPT2) expressed in the mammalian gastrointestinal tract. The use of such formulations to minimize the frequency of dosing necessary to treat patients in need of GABA analog therapy.

A number of GABA analogues are also described in Yogeeswari et al. (2006) *Recent Patents on CNS Drug Discovery* 1: 113-119, which is incorporated herein by reference for the GABA analogues described therein.

The foregoing GABA agonists, and prodrugs is intended to be illustrative and not limiting. Using the teachings provided herein, numerous other GABA agonists will be available to one of skill in the art.

Second Active Agents for Use in Combination with GABA, GABA Analogues, GABA Prodrugs, or GABA Potentiators.

As indicated above, a number of compositions, formulations, and methods that utilized GABA, GABA analogues, GABA prodrugs, and/or GABA potentiators in combination with a second active agent are contemplated. In various embodiments the second active agent can be a non-GABA therapeutic agent for the treatment of type I diabetes (e.g., a β-cell antigen vaccine, an immune-cell specific immunosuppressant, etc.), a factor that stimulates a regulatory and/or immune response, a compound having anti-inflammatory activity, a $GABA_B$ receptor agonist or partial agonist, and the like.

β-Cell Antigens.

In certain embodiments the second active compound/agent comprises a β-cell antigen (autoantigen). In this context, the β-cell antigen provides an antigen-based therapy (ABT) to prevent or inhibit autoimmune an autoimmune response (against β-cells) by inducing regulatory T-cell responses (active tolerance) or anergizing/deleting pathogenic T-cells (passive tolerance). This approach is believed to promote tolerance with little debilitation of the immune system.

Illustrative β-cell antigens believed to be useful include, but are not limited to, glutamic acid decarboxylase (GAD) or an immunogenic fragment thereof, the GAD65 isoform (GAD65) or an immunogenic fragment thereof, the GAD67 isoform or an immunogenic fragment thereof, hsp65 or an immunogenic fragment thereof, an insulin b-chain or immunogenic fragment thereof, an HSPp277 or immunogenic fragment thereof, an MHC molecule from an islet donor cell or an immunogenic fragment thereof, proinsulin or an immunogenic fragment thereof, preproinsulin or an immunogenic fragment thereof, islet-specific glucose 6 phosphatase catalytic subunit-related protein (IGRP) or an immunogenic fragment thereof, chromogranin A or an immunogenic fragment thereof, insulinoma antigen-2 or an immunogenic fragment thereof, and ZnT8 or an immunogenic fragment thereof. In various embodiments, particularly for administration to humans, the human form of the β-cell antigen (or fragment thereof) is used.

The amino acid and nucleic acid sequences of these β-cell antigens are well known and can be found for example in GenBank (see, e.g., GAD, Accession: CAA01913.1, GI: 1247492; GAD65 isoform Accession: AAB28987.1, GI: 456803; GAD67 isoform Accession: NP_000808.2, GI: 58331246; GAD25 isoform Accession: NP_038473.2, GI: 15451889, and the like).

Using the known sequences these antigens can be routinely expressed using recombinant expression methods or they can be chemically synthesized. In this regard, it is noted, for example, that the cloning and expression of GAD antigens is described by Bu et al. (1992) *Proc. Natl. Acad. Sci., USA*, 89: 2115-2119. Typically the antigen will be formulated and/or administered in conjunction with an adjuvant to increase the resulting immune response. Illustrative adjuvants include, but are not limited to aluminum salt/gel-based (alum) adjuvants, squalene, QS21, 1018 immunostimulatory sequence (ISS) and the like. Adjuvants are widely available from various commercial suppliers (see, e.g., Table 4).

TABLE 4

Illustrative commercially available vaccine adjuvants (from InvivoGen).

| Type/Name | Description |
|---|---|
| Alum and Emulsions | |
| AddaVax ™ | Vaccine Adjuvant: Squalene-Oil-in-water |
| Alhydrogel 2% | Vaccine Adjuvant: Aluminium hydroxide gel |
| IFA | Vaccine Adjuvant: Incomplete Freund's adjuvant Water-in-oil |
| PRR Ligands | |
| Flagellin FliC | TLR5 agonist-Recombinant flagellin from *S.typhimurium* |
| Gardiquimod | TLR7 agonist-Imidazoquinoline compound |
| Imiquimod | TLR7 agonist-Imidazoquinoline compound |
| MPLA VacciGrade ™ | TLR4 agonist-Monophosphoryl Lipid A |
| N-Glycolyl-MDP | NOD2 agonist-N-glycolyted muramyldipeptide |
| ODN 1826 | TLR9 agonist-CpG ODN, type B (murine) |
| ODN 2006 | TLR9 agonist-CpG ODN, type B (human) |
| Poly(I:C) | TLR3 agonist-Polyinosine-polycytidylic acid |
| R848 | TLR7/8 agonist-Imidazoquinoline compound |

The β-cell antigens (with or without adjuvant) are administered to the subject according to standard methods well known to those of skill in the art.

A new approach to vaccines has emerged in recent years, broadly termed genetic immunization. In this approach, a gene encoding the antigen of interest (e.g., a β-cell autoantigen) is operably inserted into cells in the subject to be immunized. The treated cells are transformed and produce the antigenic proteins of the pathogen. These in vivo-produced antigens then trigger the desired immune response in the host. The genetic material utilized in such genetic vaccines can be either a DNA or RNA construct. Often the polynucleotide encoding the antigen is introduced in combination with other promoter polynucleotide sequences to enhance insertion, replication, or expression of the gene.

The DNA (or RNA) vaccines encoding β-cell antigens can be introduced into the host cells of the subject by a variety of expression systems. The DNA (or RNA) can be delivered by any of a number of methods, including, but not limited to injection into the tissue of the recipient, oral or pulmonary delivery and inoculation by particle bombardment (i.e., gene gun). Any of these methods can be used to deliver the nucleic acid (e.g., DNA) as long as the nucleic acid is expressed and the desired (β-cell) antigen is made in the cell.

One common approach for the delivery of DNA vaccines is particle bombardment (e.g., using a PowderJect-XR® gene gun device described in PCT Publication WO 95/19799). Other instruments are available and known to those of skill in the art. This instrument, which delivers DNA-coated gold beads directly into epidermal cells by high-velocity particle bombardment.

The technique of accelerated particles gene delivery or particle bombardment is based on the coating of DNA to be delivered into cells onto extremely small carrier particles, which are designed to be small in relation to the cells sought to be transformed by the process. The DNA sequence containing the desired gene can be simply dried onto a small inert particle. The particle may be made of any inert material such as an inert metal (gold, silver, platinum, tungsten, etc.) or inert plastic (polystyrene, polypropylene, polycarbonate, etc.). Preferably, the particle is made of gold, platinum or tungsten. Most preferably, the particle is made of gold. Suitably, the particle is spherical and has a diameter of 0.5 to 5 microns, preferably 1 to 3 microns.

The DNA sequence containing the desired gene prepared in the form suitable for gene introduction can be simply dried onto naked gold or tungsten pellets. However, DNA molecules in such a form may have a relatively short period of stability and may tend to degrade rather rapidly due to chemical reactions with the metallic or oxide substrate of the particle itself. Thus, if the carrier particles are first coated with an encapsulating agent, the DNA strands have greatly improved stability and do not degrade significantly even over a time period of several weeks. A suitable encapsulating agent is polylysine (molecular weight 200,000) which can be applied to the carrier particles before the DNA molecules are applied. Other encapsulating agents, polymeric or otherwise, may also be useful as similar encapsulating agents, including spermidine. The polylysine is applied to the particles by rinsing the gold particles in a solution of 0.02% polylysine and then air drying or heat drying the particles thus coated. Once the metallic particles coated with polylysine were properly dried, DNA strands are then loaded onto the particles.

In certain embodiments the DNA is loaded onto the particles at a rate of between 0.5 and 30 micrograms of DNA per milligram of gold bead spheres. In certain embodiments a preferable ratio of DNA to gold is 0.5-5.0 µg of DNA per milligram of gold. A sample procedure begins with gamma irradiated (preferably about 30 kGy) tefzel tubing. The gold is weighed out into a microfuge tube, spermidine (free base) at about 0.05 M is added and mixed, and then the DNA is added. A 10% CaCl solution is incubated along with the DNA for about 10 minutes to provide a fine calcium precipitate. The precipitate carries the DNA with it onto the beads. The tubes are microfuged and the pellet resuspended and washed in 100% ethanol and the final product resuspended in 100% ethanol at 0.0025 mg/ml PVP. The gold with the DNA is then applied onto the tubing and dried.

The general approach of accelerated particle gene transfection technology is described in U.S. Pat. No. 4,945,050 to Sanford. An instrument based on an improved variant of that approach is available commercially from PowderJect Vaccines, Inc., Madison Wis., and is described in WO 95/19799. All documents cited herein supra and infra are hereby incorporated in their entirety by reference thereto. Briefly, the DNA-coated particles are deposited onto the interior surface of plastic tubing which is cut to a suitable length to form sample cartridges. A sample cartridge is placed in the path of a compressed gas (e.g., helium at a pressure sufficient to dislodge the particles from the cartridge e.g., 350-400 psi). The particles are entrained in the gas stream and are delivered with sufficient force toward the target tissue to enter the cells of the tissue.

The coated carrier particles are physically accelerated toward the cells to be transformed such that the carrier particles lodge in the interior of the target cells. This technique can be used either with cells in vitro or in vivo. At some frequency, the DNA which has been previously coated onto the carrier particles is expressed in the target cells. This gene expression technique has been demonstrated to work in prokaryotes and eukaryotes, from bacteria and yeasts to higher plants and animals. Thus, the accelerated particle method provides a convenient methodology for delivering genes into the cells of a wide variety of tissue types, and offers the capability of delivering those genes to cells in situ and in vivo without any adverse impact or effect on the treated individual.

Generally, the DNA vaccine administered may be in an amount of about 1-5 µg of DNA per dose and will depend on the subject to be treated, capacity of the subject's immune system to develop the desired immune response, and the degree of protection desired. Precise amounts of the vaccine to be administered may depend on the judgment of the practitioner and may be peculiar to each subject and antigen.

The vaccine may be given in a single dose schedule, or preferably a multiple dose schedule in which a primary course of vaccination may be with 1-10 separate doses, followed by other doses given at subsequent time intervals required to maintain and or reinforce the immune response, for example, at 1-4 months for a second dose, and if needed, a subsequent dose(s) after several months. Examples of suitable immunization schedules include: (i) 0, 1 months and 6 months, (ii) 0, 7 days and 1 month, (iii) 0 and 1 month, (iv) 0 and 6 months, or other schedules sufficient to elicit the desired immune responses expected to confer protective immunity, or reduce disease symptoms, or reduce severity of disease.

The foregoing methods are illustrative and not intended to be limiting. Methods of protein vaccination, as well as DNA vaccines and methods of use thereof are well known to those of skill in the art (see, e.g., Robinson and Pertmer (2000) *Adv. Virus Res.* 55: 1-74; Alarcon et al. (1999) *Adv. Parasitol.* 42: 343-410; Tang et al. (1992) *Nature* 356 (6365): 152-154; and the like).

A factor that Stimulates a Regulatory and/or Immune Response or that is an Immune-Cell Specific Immunosuppressant.

In certain embodiments the second active compound/agent comprises one or more compounds for "immunoregulation", i.e., for the control of an undesired immune response. In various embodiments the compound for immunoregulation includes certain immunosuppressants, immunostimulants and tolerogens.

In certain embodiments the compound(s) for immune regulation include agents that inhibit a cell-based immune response (e.g., inhibit T and/or B cells).

In certain embodiments the compound(s) for immune regulation include, but are not limited to an antigen that has a therapeutic effect in type I diabetes.

In certain embodiments the compound(s) for immune regulation include, but are not limited to, an anti-CD3 antibody, exendin-4, and/or a pro-insulin therapeutic. In certain embodiments the anti-CD3 antibody comprises a non-activating anti-CD3 monoclonal antibody (or fragment thereof) (e.g., comprises a hOKT3γ1(Ala-Ala) monoclonal antibody or an anti-CD3 F(ab')₂).

In certain embodiments the compound(s) for immune regulation include, but are not limited to, one or more compounds selected from the group consisting of Alpha-1 Antitrypsin (AAT), Canakinumab, Diamyd, Exsulin, LCT, Lisofylline, Rituximab, Xoma 052, DiaPep277, Prochymal, Reparixin, Thymoglobulin, Ilaris (canakinumab), Januvia and Prevacid, Alpha-antitrypsin, and/or Amevive (alefacept).

In certain embodiments the compound(s) for immune regulation include, but are not limited to, one or more compounds selected from the group consisting of an interleukin-2 or an analogue thereof, TGFβ or an analogue thereof, IL-10 or an analogue thereof, an IL-6 antagonist, an IL-23 antagonist, a CD25 antagonist, an anti-IL-6 antibody, anti-IL-23 antibody, and an anti-CD25 antibody.

In certain embodiments the compound(s) for immune regulation include, but are not limited to, one or more compounds selected from the group consisting of selected from the group consisting of an anti-CD3 antibody, anti-TNF, anti-IFN, CTLA-4 fused to Ig, anti-thymocyte globulin, anti-CD3 antibody (muromonab or Otelixizumab), sirolimus, and mycophenolate.

In certain embodiments the compound(s) for immune regulation include, but are not limited to, one or more compounds selected from the group consisting of Azathioprine, Mycophenolic acid, Leflunomide, Teriflunomide, methotrexate, FKBP/Cyclophilin/Calcineurin, Tacrolimus, Ciclosporin, Pimecrolimus, Abetimus, Gusperimus, Thalidomide, Lenalidomide, Sirolimus, Deforolimus, Everolimus, Temsirolimus, Zotarolimus, Biolimus A9, and Anakinra.

In certain embodiments the compound(s) for immune regulation include, but are not limited to, one or more compounds selected from the group consisting of anti-Complement component 5 (Eculizumab), anti-TNFs (Infliximab, Adalimumab, Certolizumab pegol, Afelimomab, Golimumab, Nerelimomab), anti-Interleukin 5 (Mepolizumab), anti-imunoglobulin E (Omalizumab), anti-Interferon (Faralimomab), anti-IL-6 (Elsilimomab), anti-IL-12 and anti-IL-23 (Lebrikizumab, Ustekinumab), anti-CD3 (Muromonab-CD3, Otelixizumab, Teplizumab, Visilizumab), anti-CD4 (Clenoliximab, Keliximab, Zanolimumab), anti-CD11a (Efalizumab), anti-CD18 (Erlizumab), anti-CD20 (Afutuzumab, Rituximab, Ocrelizumab, Pascolizumab), anti-CD23 (Lumiliximab), anti-CD40 (Teneliximab, Toralizumab), anti-CD62L/L-selectin (Aselizumab), anti-CD80 (Galiximab), anti-CD147/Basigin (Gavilimomab), anti-CD154 (Ruplizumab), anti-BLyS (Belimumab), CTLA-4 (Ipilimumab, Tremelimumab), CAT (Bertilimumab, Lerdelimumab, Metelimumab), anti-Integrin (Natalizumab), anti-Interleukin-6 receptor (Tocilizumab), anti-LFA-1 (Odulimomab), anti-IL-2 receptor/CD25 (Basiliximab, Daclizumab, Inolimomab), anti-T-lymphocyte (Zolimomab aritox), Atorolimumab, Cedelizumab, Dorlixizumab, Fontolizumab, Gantenerumab, Gomiliximab, Maslimomab, Morolimumab, Pexelizumab, Reslizumab, Rovelizumab, Siplizumab, Talizumab, Telimomab aritox, Vapaliximab, Vepalimomab, Anti-thymocyte globulin, Anti-lymphocyte globulin, CTLA-4 (Abatacept, Belatacept), TNF inhibitor (Etanercept, Pegsunercept), Aflibercept, Alefacept, and Rilonacept.

GABA$_B$ Receptor Agonists or Partial Agonists.

In certain embodiments the second active compound/agent comprises a compound (agent) that has agonistic activity at the GABA$_B$ receptor. In certain embodiments the GABA$_B$ receptor activity is specific to the GABA$_B$ receptor.

The GABA$_B$ receptor agonist baclofen ((RS)-4-amino-3-(4-chlorophenyl)butanoic acid) (brand names KEMSTRO®, LIORESAL®, AND GABLOFEN®) has been the most studied of the GABA analogs.

Other GABA$_B$ receptor agonists are known and include for example, (3-amino-2(S)-hydroxypropyl)methylphosphinic acid (CGP 44532), 3-aminopropyl(methyl)phosphinic acid (SKF 97541), 3-aminopropylphosphonic acid (3-APA) 3-(Aminopropyl)methyl phosphinic acid (see, e.g., EP 0356128), and 3-aminopropanephosphonous acids as described in U.S. Pat. No. 5,04,826 (EP 0181833). In certain embodiments the 3-aminopropanephosphonous acids have the formula:

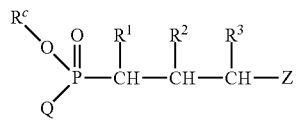

in which one of the groups $R^1$, $R^2$ and $R^3$ represents hydrogen, $C_{1-9}$ alkyl, $C_{3-6}$-cycloalkyl, phenyl either unsubstituted or substituted by halogen, $C_{1-4}$ alkyl, $C_{1-4}$ alkoxy and/or trifluoromethyl, or phenyl-$C_{1-4}$ alkyl either unsubstituted or substituted in the phenyl moiety by halogen, $C_{1-4}$ alkyl, $C_{1-4}$ alkoxy and/or trifluoromethyl, and the other two are hydrogen, Q denotes a group having the formula —C($C_{1-4}$ alkyl)(OR$^a$)OR$^b$, in which R$^a$ and R$^b$ are each $C_{1-4}$ alkyl, R$^c$ is $C_{1-4}$ alkyl and Z denotes —NH$_2$, or a pharmaceutically acceptable salt thereof. In certain embodiments, the 3-aminopropanephosphonous acid as the formula:

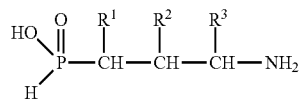

where $R^1$, $R^2$, and $R^3$ are as denoted in Table 5.

TABLE 5

Illustrative 3-aminopropanephosphonous acids.

| Compound | $R^1$ | $R^2$ | $R^3$ |
|---|---|---|---|
| a | H | 4-chlorophenyl | H |
|   |   |   | RS, R, or S forms |
| b | H | 2-methylphenyl | H |
| c | H | 4-bromophenyl | H |
| d | H | 2-methoxyphenyl | H |
| e | H | 3,4-dimethoxyphenyl | H |
| f | H | 4-trifluoromethylphenyl | H |
| g | H | 3,4-dichlorophenyl | H |
| h | H | sec-butyl | H |
| i | H | n-octyl | H |
| j | H | 4-chlorobenzyl | H |

Other suitable GABAB agonists include, but are not limited to substituted aminoalkylphosphoic acids as described in EP 0399949, and compounds according to formulas I, II, or III in EP 0463969 (U.S. Pat. No. 7,319,095) according to Formulas I, II, or III therein. Certain illustrative species of the latter include (3-amino-2-fluoropropyl)phosphinic acid; (2R)-(3-amino-2-fluoropropyl)phosphinic acid; (2S)-(3-amino-2-fluoropropyl)phosphinic acid; (3-amino-2-fluoro-1-methylpropyl)phosphinic acid; (3-amino-2-oxopropyl)phosphinic acid; (2S)-(3-amino-2-hydroxypropyl) phosphinic acid; (R)-(3-amino-2-hydroxypropyl)phosphinic acid; and (3-amino-1-fluoro-2-hydroxypropyl)phosphinic acid (Formula I) or (3-amino-2-fluoropropyl)sulphinic acid, (2S)-(3-amino-2-fluoropropyl)sulphinic acid, (2R)-(3-amino-2-fluoropropyl)sulphinic acid, (2S)-(3-amino-2-hydroxypropyl)sulphinic acid, (2R)-(3-amino-2-hydroxypropyl)sulphinic acid and (3-amino-2-oxopropyl)sulphinic acid (Formula III).

For a review on the chemistry of $GABA_B$ modulators, see Forest, W. and Mickel, S. J. in: The GABA Receptors, pp. 271-296 (Eds. S. J. Enna and N. G. Bowery, Humana Press Inc., Totowa, N.J., U.S.A. 1997).

These $GABA_B$ agonists are intended to be illustrative and not limiting. Using the teachings provided herein, numerous other $GABA_B$ agonists will be available to one of skill in the art Pharmaceutical Formulations The active agents described herein (e.g., the "first" agent comprising GABA, a GABA analogue, a GABA agonist, a GABA or GABA agonist prodrug, and/or a GABA potentiator and, when present, the other therapeutic agents (the "second agent") described herein are typically administered in the form of pharmaceutical compositions. In certain embodiments the first agent and the "second" agent are administered separately (particularly where different delivery modalities are required. In certain embodiments the first agent and the "second" agent are administered together and, in certain embodiments, as a combined formulation. Accordingly in various embodiments combined formulations comprising any one or more "first agents" (first compounds) described herein and any one or more "second agents" (second compounds) described herein are contemplated.

The various active agents described herein can be administered by a variety of routes including, but not limited to, oral, rectal, subcutaneous, intravenous, intramuscular and intranasal. In certain embodiments oral administration of these compounds and compositions is particularly preferred. Such compositions are prepared in a manner well known in the pharmaceutical art and comprise at least one active compound.

In various embodiments pharmaceutical compositions are contemplated that comprise, as the active ingredient a first agent (e.g., GABA, a GABA analogue, a GABA agonist, a GABA or GABA agonist prodrug, and/or a GABA potentiators. In certain embodiments the GABA agonist or prodrug is a $GABA_A$ receptor specific or preferential agonist or prodrug. In certain embodiments the composition comprises the first agent and/or one or more second agent(s) described herein.

In making the compositions of this invention, the active ingredient(s) can be mixed with an excipient, diluted by an excipient or enclosed within such a carrier, which can be in the form of a capsule, sachet, paper or other container. When the excipient serves as a diluent, it can be a solid, semi-solid, or liquid material, which acts as a vehicle, carrier or medium for the active ingredient(s). Thus, the compositions can be in the form of tablets, pills, powders, lozenges, sachets, cachets, elixirs, suspensions, emulsions, solutions, syrups, aerosols (as a solid or in a liquid medium), soft and hard gelatin capsules, suppositories, sterile injectable solutions, and sterile packaged powders.

In preparing a formulation, it may be necessary to mill the active compound(s) to provide the appropriate particle size prior to combining with other ingredients. If the active compound(s) are substantially insoluble, they can, for example, be milled to a particle size of less than 200 mesh. If the active compound(s) are substantially water soluble, the particle size is normally adjusted by milling to provide a substantially uniform distribution in the formulation, e.g. about 40 mesh.

Some examples of suitable excipients include, but are not limited to lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions can be formulated so as to provide quick, sustained or delayed release of the active ingredient after administration to the patient by employing procedures known in the art.

In certain embodiments the compositions are formulated in a unit dosage form, each dosage containing, for example, from about 0.1 to about 5000 mg, more usually about 10 to about 2000 mg, of the active ingredient(s). The term "unit dosage forms" refers to physically discrete units suitable as unitary dosages for human subjects and other animals, each unit containing a predetermined quantity of active material calculated to produce the desired therapeutic effect, in association with a suitable pharmaceutical excipient.

In various embodiments the active compound(s) (e.g. GABA receptor agonists) are effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient(s) are mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 mg to about 2 g of the active ingredient of the present invention.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include, but are not limited to, solutions and suspensions in pharmaceutically acceptable, aqueous or organic solvents or mixtures thereof, and powders. The liquid or solid compositions may contain suitable pharmaceutically acceptable excipients as described supra. In certain embodiments the compositions are administered by the oral or nasal respiratory route. Compositions in pharmaceutically acceptable solvents can be nebulized by use of inert gases. Nebulized solutions may be breathed directly from the nebulizing device or the nebulizing device may be attached to a face masks tent, or intermittent positive pressure breathing machine. Solution, suspension, or powder compositions can be administered, preferably orally or nasally, from devices which deliver the formulation in an appropriate manner.

In certain embodiments GABA, more preferably one or more GABA receptor agonists, may be delivered via sustained release systems, preferably oral sustained release systems. Sustained release dosage forms for oral administration are described in greater detail below.

The present methods described herein can be practiced with a number of different dosage forms, that can be adapted to provide sustained release of the drug or prodrug upon oral administration.

In one illustrative embodiment the dosage form comprises beads that on dissolution or diffusion release the prodrug over an extended period of hours, preferably, over a period of at least 6 hours, more preferably, over a period of at least 8 hours and most preferably, over a period of at least 12 hours. The prodrug-releasing beads may have a central composition or core comprising a prodrug and pharmaceutically acceptable vehicles, including an optional lubricant, antioxidant and buffer. The beads can be medical preparations with, for example, a diameter of about 1 to 2 mm. Individual beads can comprise doses of the drug or prodrug, for example, doses of up to about 40 mg of drug or prodrug. The beads, in one embodiment, are formed of non-cross-linked materials to enhance their discharge from the gastrointestinal tract. The beads may be coated with a release rate-controlling polymer that gives a timed release profile.

In certain embodiments time release beads can be manufactured into a tablet for therapeutically effective drug or prodrug administration. The beads can be made into matrix tablets by the direct compression of a plurality of beads coated with, for example, an acrylic resin and blended with excipients such as hydroxypropylmethyl cellulose. The manufacture of beads has been disclosed in the art (see, e.g., Lu (1994) *Int. J. Pharm.*, 112: 117-124; Pharmaceutical Sciences by Remington, 14th ed, pp 1626-1628 (1970); Fincher (1968) *Pharm. Sci.* 57: 1825-1835, and the like) as has the manufacture of tablets and other delivery modalities (see, e.g., Pharmaceutical Sciences, by Remington, 17th Ed, Ch. 90, pp 1603-1625 (1985)).

In certain embodiments, an oral sustained release pump may be used (see Langer, supra; Sefton (1987) *CRC Crit Ref Biomed Eng.* 14: 201; Saudek et al. (1989) *N. Engl. J Med.* 321: 574, and the like).

In another embodiment, polymeric materials can be used (see "Medical Applications of Controlled Release," Langer and Wise (eds.), CRC Press, Boca Raton, Fla. (1974); "Controlled Drug Bioavailability," Drug Product Design and Performance, Smolen and Ball (eds.), Wiley, New York (1984); Ranger and Peppas (1983) *J Macromol. Sci. Rev. Macromol Chem.* 23: 61; also Levy et al. (1985) *Science* 228: 190; During et al. (1989) *Ann. Neurol.* 25: 351; Howard et al. (1989) *J. Neurosurg.* 71: 105, etc.). In certain illustrative embodiments, polymeric materials are used for oral sustained release delivery. Suitable polymers include, but are not limited to sodium carboxymethylcellulose, hydroxypropylcellulose, hydroxypropylmethylcellulose and hydroxyethylcellulose (most preferred, hydroxypropylmethylcellulose, and the like. Other suitable cellulose ethers have been described (see, e.g., Alderman (1984) *Int. J. Pharm. Tech. & Prod. Mfr.*, 5(3) 1-9). Factors affecting drug release are well known to the skilled artisan and have been described in the art (see, e.g., Bamba et al. (1979) *Int. J. Pharm.*, 2: 307).

In another illustrative embodiment, enteric-coated preparations can be used for oral sustained release administration. Suitable coating materials include polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In certain embodiments drug-releasing lipid matrices can be used for oral sustained release administration. One illustrative example is when solid microparticles of the drug or prodrug are coated with a thin controlled release layer of a lipid (e.g., glyceryl behenate and/or glyceryl palmitostearate) (see, e.g., U.S. Pat. Nos. 6,375,987 and 6,379,700). The lipid-coated particles can optionally be compressed to form a tablet. Another controlled release lipid-based matrix material which is suitable for sustained release oral administration comprises polyglycolized glycerides (see, e.g., U.S. Pat. No. 6,171,615).

In yet another illustrative embodiment, prodrug-releasing waxes can be used for oral sustained release administration. Examples of suitable sustained drug or prodrug-releasing waxes are disclosed in U.S. Pat. No. 3,402,240 (carnauba wax, candedilla wax, esparto wax and ouricury wax); U.S. Pat. No. 4,820,523 (hydrogenated vegetable oil, bees wax, caranuba wax, paraffin, candelillia, ozokerite and mixtures thereof); and U.S. Pat. No. 4,421,736 (mixture of paraffin and castor wax).

In still another embodiment, osmotic delivery systems are used for oral sustained release administration (see, e.g., Verma et al. (2000) *Drug Dev. Ind. Pharm.*, 26: 695-708). In certain embodiments OROSa systems made by Alza Corporation, Mountain View, Calif. are used for oral sustained release delivery devices (see, e.g., U.S. Pat. Nos. 3,845,770 and 3,916,899).

In yet another embodiment, a controlled-release system can be placed in proximity of the target of the prodrug of the GABA agonist, thus requiring only a fraction of the systemic dose (see, e.g., Goodson, in "Medical Applications of Controlled Release," supra, vol. 2, pp. 115-138 (1984)). Other controlled-release systems discussed in Langer, 1990, Science 249:1527-1533 may also be used.

In certain embodiments the dosage form comprises a prodrug of a $GABA_A$ receptor agonist analog coated on a polymer substrate. The polymer can be an erodible, or a nonerodible polymer. The coated substrate may be folded onto itself to provide a bilayer polymer drug dosage form. For example prodrug of a $GABA_A$ receptor agonist can be coated onto a polymer such as a polypeptide, collagen, gelatin, polyvinyl alcohol, polyorthoester, polyacetyl, or a polyorthocarbonate and the coated polymer folded onto itself to provide a bilaminated dosage form. In operation, the bioerodible dosage form erodes at a controlled rate to dispense the prodrug over a sustained release period. Illustrative biodegradable polymer comprise a member selected from the group consisting of biodegradable poly(amides), poly(amino acids), poly(esters), poly(lactic acid), poly(glycolic acid), poly(carbohydrate), poly(orthoester), poly(orthocarbonate), poly(acetyl), poly(anhydrides), biodegradable poly(dehydropyrans), and poly(dioxinones) which are known in the art (Rosoff, Controlled Release of Drugs, Chap. 2, pp. 53-95 (1989); and in U.S. Pat. Nos. 3,811,444; 3,962,414; 4,066,747, 4,070,347; 4,079,038; and 4,093,709).

In certain embodiments dosage form comprises a prodrug loaded into a polymer that releases the prodrug by diffusion through a polymer, or by flux through pores or by rupture of a polymer matrix. The drug delivery polymeric dosage form comprises a concentration of 10 mg to 2500 mg homogenously contained in or on a polymer. The dosage form comprises at least one exposed surface at the beginning of dose delivery. The non-exposed surface, when present, is coated with a pharmaceutically acceptable material impermeable to the passage of a prodrug. The dosage form may be manufactured by procedures known in the art. An example of providing a dosage form comprises blending a pharmaceutically acceptable carrier like polyethylene glycol, with a known dose of prodrug at an elevated temperature, like 37° C., and adding it to a silastic medical grade elastomer with a cross-linking agent, for example, octanoate, followed by casting in a mold. The step is repeated for each optional successive layer. The system is allowed to set for 1 hour, to provide the dosage form. Representative polymers for manufacturing the dosage form comprise a member selected from the group consisting of olefin, and vinyl polymers, addition polymers, condensation polymers, carbohydrate polymers, and silicon polymers as represented by polyethylene, polypropylene, polyvinyl acetate, polymethylacrylate, polyisobutylmethacrylate, poly alginate, polyamide and polysilicon. The polymers and procedures for manufacturing them have been described in the art (see, e.g., Coleman et al., Polymers 1990, 31, 1187-1231; Roerdink et al. (1989) *Drug Carrier Systems,* 9: 57-10; Leong et al. (1987) *Adv. Drug Delivery Rev.* 1: 199-233; Roff et al. (1971) *Handbook of Common Polymers*, CRC Press; U.S. Pat. No. 3,992,518).

In certain embodiments the dosage from comprises a plurality of tiny pills. The tiny time-released pills provide a number of individual doses for providing various time doses for achieving a sustained-release drug/prodrug delivery profile over an extended period of time e.g., up to 24 hours. The matrix comprises a hydrophilic polymer (e.g., a polysaccharide, agar, agarose, natural gum, alkali alginate including sodium alginate, carrageenan, fucoidan, furcellaran, laminaran, hypnea, gum arabic, gum ghatti, gum karaya, grum tragacanth, locust bean gum, pectin, amylopectin, gelatin), and a hydrophilic colloid. The hydrophilic matric comprises a plurality (e.g., 4 to 50 or 100) of tiny pills, each tiny pill comprising a dose population of, for example, from 10 ng, 0.5 mg, 1 mg, 1.2 mg, 1.4 mg, 1.6 mg, 5.0 mg etc. In certain embodiments the tiny pills comprise a release rate-controlling wall of 0.001 up to 1.0 mm thickness to provide for the timed release of drug/prodrug. Illustrative wall forming materials include, but are not limited to, a triglyceryl ester selected from the group consisting of glyceryl tristearate, glyceryl monostearate, glyceryl dipalmitate, glyceryl laureate, glyceryl didecenoate and glyceryl tridenoate. Other illustrative wall forming materials comprise polyvinyl acetate, phthalate, methylcellulose phthalate and microporous olefins. Procedures for manufacturing tiny pills are disclosed in U.S. Pat. Nos. 4,434,153; 4,721,613; 4,853,229; 2,996,431; 3,139,383 and 4,752,470.

In certain embodiments the dosage form comprises an osmotic dosage form, which comprises a semipermeable wall that surrounds a therapeutic composition comprising the drug or prodrug. In use within a patient, the osmotic dosage form comprising a homogenous composition imbibes fluid through the semipermeable wall into the dosage form in response to the concentration gradient across the semipermeable wall. The therapeutic composition in the dosage form develops osmotic energy that causes the therapeutic composition to be administered through an exit from the dosage form over a prolonged period of time up to 24 hours (or even in some cases up to 30 hours) to provide controlled and sustained prodrug release. These delivery platforms can provide an essentially zero order delivery profile as opposed to the spiked profiles of immediate release formulations.

In certain embodiments the dosage form comprises another osmotic dosage form comprising a wall surrounding a compartment, the wall comprising a semipermeable polymeric composition permeable to the passage of fluid and substantially impermeable to the passage of drug/prodrug present in the compartment, a prodrug-containing layer composition in the compartment, a hydrogel push layer composition in the compartment comprising an osmotic formulation for imbibing and absorbing fluid for expanding in size for pushing the prodrug composition layer from the dosage form, and at least one passageway in the wall for releasing the prodrug composition. The method delivers the drug/prodrug by imbibing fluid through the semipermeable wall at a fluid imbibing rate determined by the permeability of the semipermeable wall and the osmotic pressure across the semipermeable wall causing the push layer to expand, thereby delivering the prodrug from the dosage form through the exit passageway to a patient over a prolonged period of time (e.g., up to 24 or even 30 hours). In certain embodiments the hydrogel layer composition may comprise 10 mg to 1000 mg of a hydrogel such as a member selected from the group consisting of a polyalkylene oxide of 1,000,000 to 8,000,000 which are selected from the group consisting of a polyethylene oxide of 1,000,000 weight-average molecular weight, a polyethylene oxide of 2,000,000 molecular weight, a polyethylene oxide of 4,000,000 molecular weight, a polyethylene oxide of 5,000,000 molecular weight, a polyethylene oxide of 7,000,000 molecular weight and a polypropylene oxide of the 1,000,000 to 8,000,000 weight-average molecular weight; or 10 mg to 1000 mg of an alkali carboxymethylcellulose of 10,000 to 6,000,000 weight average molecular weight, such as sodium carboxymethylcellulose or potassium carboxymethylcellulose. In certain embodiments the hydrogel expansion layer comprises 0.0 mg to 350 mg, e.g., 0.1 mg to 250 mg of a hydroxyalkylcellulose of 7,500 to 4,500,00 weight-average molecular weight (e.g., hydroxymethylcellulose, hydroxyethylcellulose, hydroxypropylcellulose, hydroxybutylcellulose or hydroxypentylcellulose); e.g, 1 mg to 50 mg of an osmagent selected from the group consisting of sodium chloride, potassium chloride, potassium acid phosphate, tartaric acid, citric acid, raffinose, magnesium sulfate, magnesium chloride, urea, inositol, sucrose, glucose and sorbitol; 0 to 5 mg of a colorant, such as ferric oxide; 0 mg to 30 mg, in a present manufacture, 0.1 mg to 30 mg of a hydroxypropylalkylcellulose of 9,000 to 225,000 average-number molecular weight, selected from the group consisting of hydroxypropylethylcellulose, hydroxypropypentylcellulose, hydroxypropylmethylcellulose, and hydropropylbutylcellulose; 0.00 to 1.5 mg of an antioxidant selected from the group consisting of ascorbic acid, butylated hydroxyanisole, butylatedhydroxyquinone, butylhydroxyanisol, hydroxycomarin, butylated hydroxytoluene, cephalm, ethyl gallate, propyl gallate, octyl gallate, lauryl gallate, propyl-hydroxybenzoate, trihydroxybutylrophenone, dimethylphenol, dibutylphenol, vitamin E, lecithin and ethanolamine; and 0.0 mg to 7 mg of a lubricant selected from the group consisting of calcium stearate, magnesium stearate, zinc stearate, magnesium oleate, calcium palmitate, sodium suberate, potassium laureate, salts of fatty acids, salts of alicyclic acids, salts of aromatic acids, stearic acid, oleic acid, palmitic acid, a mixture of a salt of a fatty, alicyclic or aromatic acid, and a fatty, alicyclic, or aromatic acid.

In certain osmotic dosage forms, the semipermeable wall comprises a composition that is permeable to the passage of fluid and impermeable to the passage of drug/prodrug. The wall is nontoxic and can comprise a polymer selected from the group consisting of a cellulose acylate, cellulose diacylate, cellulose triacylate, cellulose acetate, cellulose diacetate and cellulose triacetate. In certain embodiments the wall comprises 75 wt % (weight percent) to 100 wt % of the cellulosic wall-forming polymer; or, the wall can comprise additionally 0.01 wt % to 80 wt % of polyethylene glycol, or 1 wt % to 25 wt % of a cellulose ether selected from the group consisting of hydroxypropylcellulose or a hydroxypropylalkycellulose such as hydroxypropylmethylcellulose. In certain embodiments the total weight percent of all components comprising the wall is equal to 100 wt %. The internal compartment comprises the drug/prodrug-containing composition alone or in layered position with an expandable hydrogel composition. The expandable hydrogel composition in the compartment increases in dimension by imbibing the fluid through the semipermeable wall, causing the hydro gel to expand and occupy space in the compartment, whereby the drug composition is pushed from the dosage form. The therapeutic layer and the expandable layer can act together during the operation of the dosage form for the release of prodrug to a patient over time. In certain embodiments the dosage form comprises a passageway in the wall that connects the exterior of the dosage form with the internal compartment. In certain embodiments the osmotic powered dosage form can deliver drug/prodrug from the dosage form to the patient at a zero order rate of release over a period of up to about 24 hours.

In certain embodiments the expression "passageway" comprises means and methods suitable for the metered release of the drug/prodrug from the compartment of the dosage form. The exit means can comprise at least one passageway, including orifice, bore, aperture, pore, porous element, hollow fiber, capillary tube, channel, porous overlay, or porous element that provides for the osmotic controlled release of drug/prodrug. The passageway includes a material that erodes or is leached from the wall in a fluid environment of use to produce at least one controlled-release dimensioned passageway. Representative materials suitable for forming a passageway, or a multiplicity of passageways comprise a leachable poly(glycolic) acid or poly(lactic) acid polymer in the wall, a gelatinous filament, poly(vinyl alcohol), leach-able polysaccharides, salts, and oxides. A pore passageway, or more than one pore passageway, can be formed by leaching a leachable compound, such as sorbitol, from the wall. The passageway possesses controlled-release dimensions, such as round, triangular, square and elliptical, for the metered release of prodrug from the dosage form. The dosage form can be constructed with one or more passageways in spaced apart relationship on a single surface or on more than one surface of the wall. The expression "fluid environment" denotes an aqueous or biological fluid as in a human patient, including the gastrointestinal tract. Passageways and equipment for forming passageways are disclosed in U.S. Pat. Nos. 3,845,770; 3,916,899; 4,063,064; 4,088,864 and 4,816,263. Passageways formed by leaching are disclosed in U.S. Pat. Nos. 4,200,098 and 4,285,987.

Regardless of the specific form of sustained release oral dosage form used, in certain embodiments the drug/prodrug is preferably released from the dosage form over a period of at least about 6 hours, more preferably, over a period of at least about 8 hours, and most preferably, over a period of at least about 1.2 hours. Further, in certain embodiments, the dosage form preferably releases from 0 to 20% of the drug/prodrug in 0 to 2 hours, from 20 to 50% of the prodrug in 2 to 12 hours, from 50 to 85% of the prodrug in 3 to 20 hours and greater than 75% of the prodrug in 5 to 18 hours. In certain embodiments the sustained release oral dosage form further provides a concentration of, e.g., the $GABA_A$ receptor agonist, in the blood plasma of the patient over time, which curve has an area under the curve (AUC) that is proportional to the dose of the prodrug of $GABA_A$ receptor agonist administered, and a maximum concentration Cmax. In certain embodiments the $C_{max}$ is less than 75%, and is preferably, less than 60%, of the $C_{max}$ obtained from administering an equivalent dose of the drug/prodrug from an immediate release oral dosage form, and the AUC is substantially the same as the AUC obtained from administering an equivalent dose of the prodrug from an immediate release oral dosage form.

In certain embodiments the dosage forms are administered twice per day (more preferably, once per day).

It will be noted that, particular with respect to antigens, as explained above, the antigen need not be provided in a typical vaccination formulation. For example, the "antigen" may be delivered through a DNA plasmid vector that directs the expression of the protein. DNA vaccines and method of use thereof are well known to those of skill in the art (see, e.g., Robinson and Pertmer (2000) *Adv. Virus Res.* 55: 1-74; Alarcon et al. (1999) *Adv. Parasitol.* 42: 343-410; Tang et al. (1992) *Nature* 356 (6365): 152-154; and the like).

Kits.

In another embodiment this invention provides for the practice of any of the methods described herein. In certain embodiments the kits comprise a container containing GABA or a GABA receptor agonists (first active agent(s)), and a container containing a second active agent as described herein (e.g., a GAD or other β-cell antigen). In certain embodiments the active agent(s) can be provided in unit dosage formulation(s) (e.g., suppository, tablet, caplet, patch, etc.) and/or may be optionally combined with one or more pharmaceutically acceptable excipients.

In addition, the kits optionally include labeling and/or instructional materials providing directions (i.e., protocols) for the practice of the methods of this invention. Certain labeling or instructional materials describe the use of one or more active agent(s) described herein to ameliorate one or more symptoms or disorders associated with metabolic syndrome, and/or delay the onset of type I diabetes, and/or slow the progression of type I diabetes, and/or reduce the severity of type I diabetes, and/or reverse type I diabetes in a mammal; and/or to promote transplanted islet cell survival in a mammal; and/or to delay the onset of hyperglycemia, and/or to slow the progression of hyperglycemia, and/or to reduce the severity of hyperglycemia, and/or to reverse hyperglycemia in a mammal; and/or to promote transplanted islet cell survival in a mammal having type I diabetes or at risk for type I diabetes who is a recipient of transplanted islet cells; and/or to delay the onset of an immune response, and/or slow the progression of an immune response, and/or reduce the severity of an immune response, and/or suppress an immune response in a mammal; and/or to protect beta-cells in a mammal from oxidative stress induced apoptosis. The labeling or instructional materials may also, optionally, teach preferred dosages/therapeutic regiment, counter indications and the like.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

GABA in Pre-Obese Mammals Reduces Insulin Resistance, Improves Glucose Tolerance, and Reduces Obesity This example demonstrates that including GABA in the diet of mice that are developing obesity reduces their insulin resistance, improves their glucose tolerance, reduces immune (e.g., macrophage) infiltrates into their adipose tissue, reduces the mass of adipocytes, and reduces obesity. Accordingly, GABA treatment has relevance for ameliorating risk factors of metabolic syndrome, cardiovascular disease and T2D.

Mice were fed high fat diet (HFD) or "western diet" causing them to gain weight, become obese, and develop glucose intolerance, insulin resistance, and metabolic syndrome. The mice were provided either normal water, or water that contained GABA (6 mg/ml). The weight, food intake, water intake, glucose tolerance, insulin sensitivity and blood glucose levels of the mice was monitored over 5 months.

Figure 2:
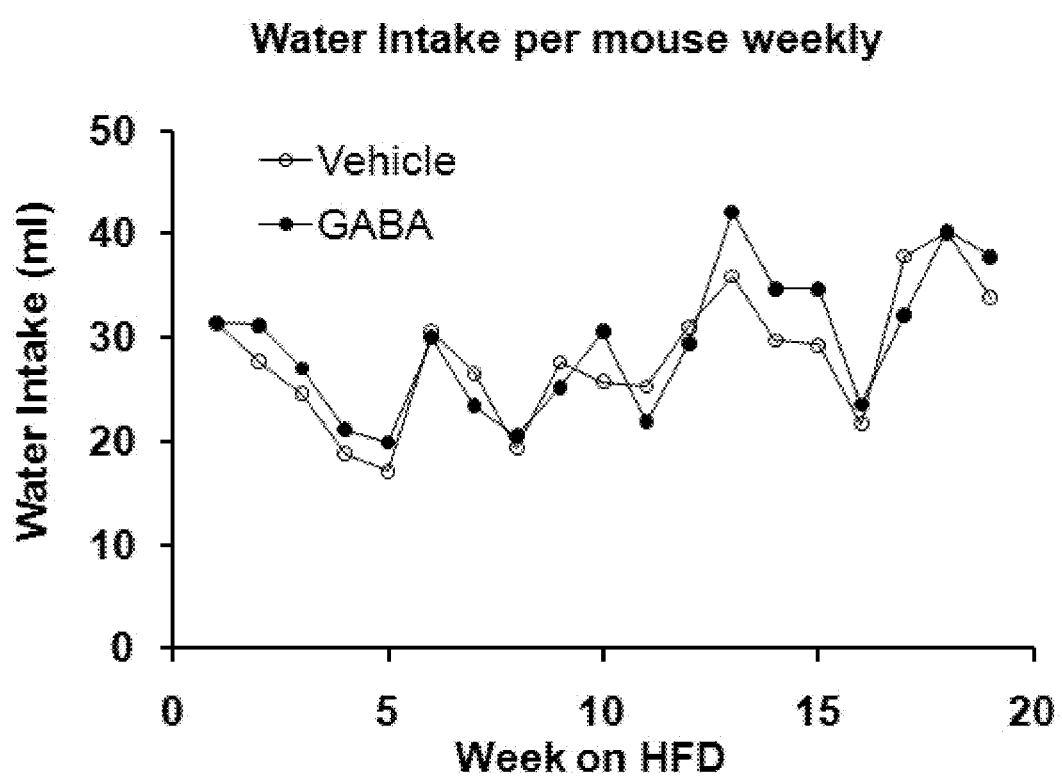
FIG. 2 illustrates the effect of GABA on water intake on HFD-fed mice.
Figure 3:
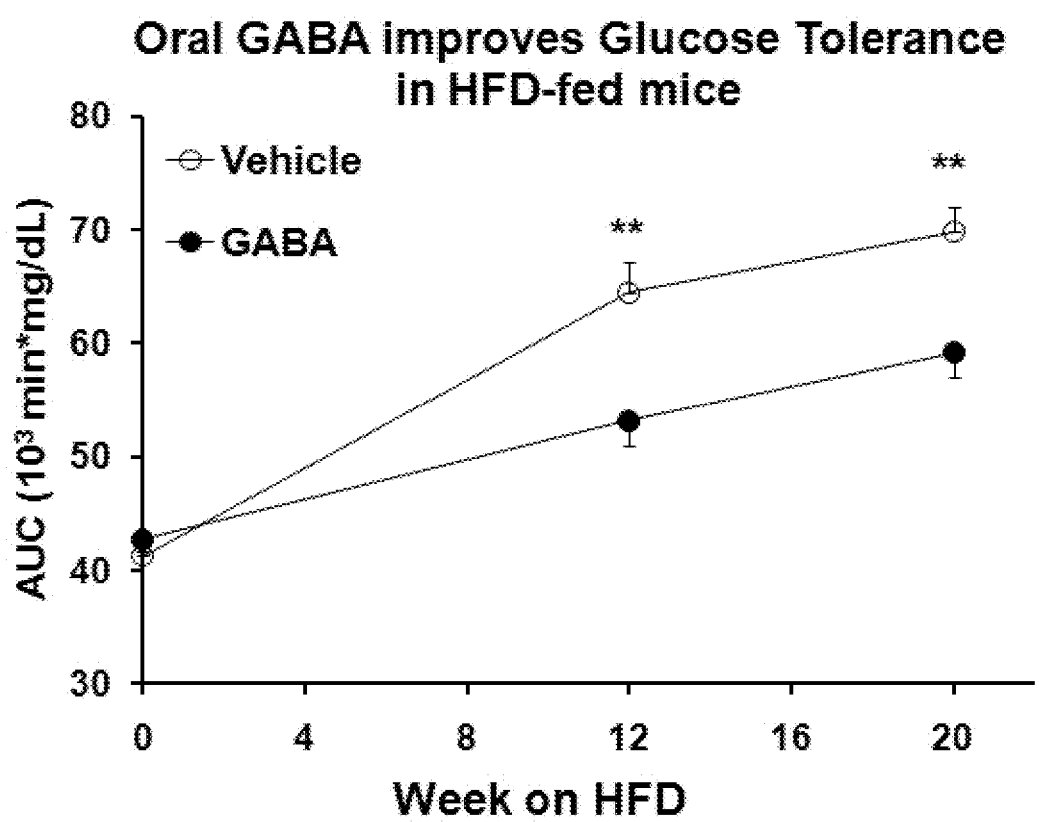
FIG. 3 shows that GABA improves glucose tolerance in HFD-fed mice.
Figure 4:
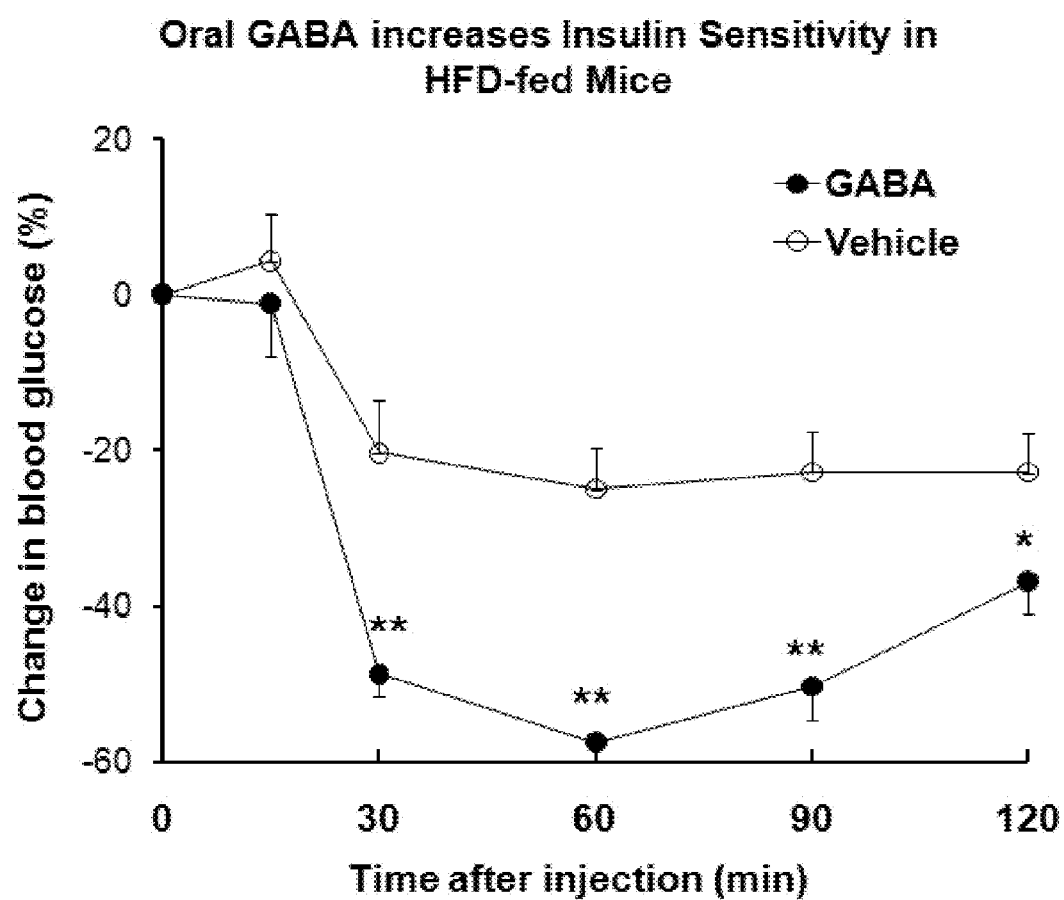
FIG. 4 shows that GABA improve insulin sensitivity in HFD-fed.
Figure 5:
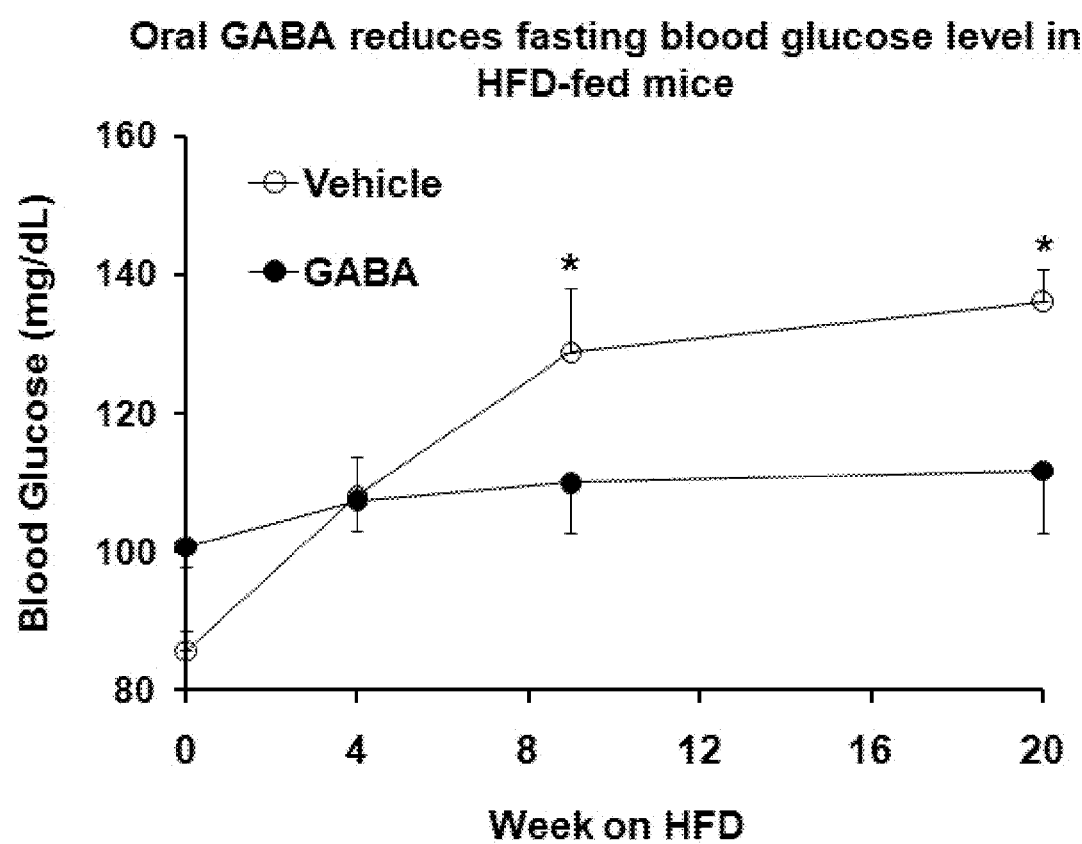
FIG. 5 shows that GABA reduces fasting blood glucose levels in HFD-fed mice.
Figure 6:
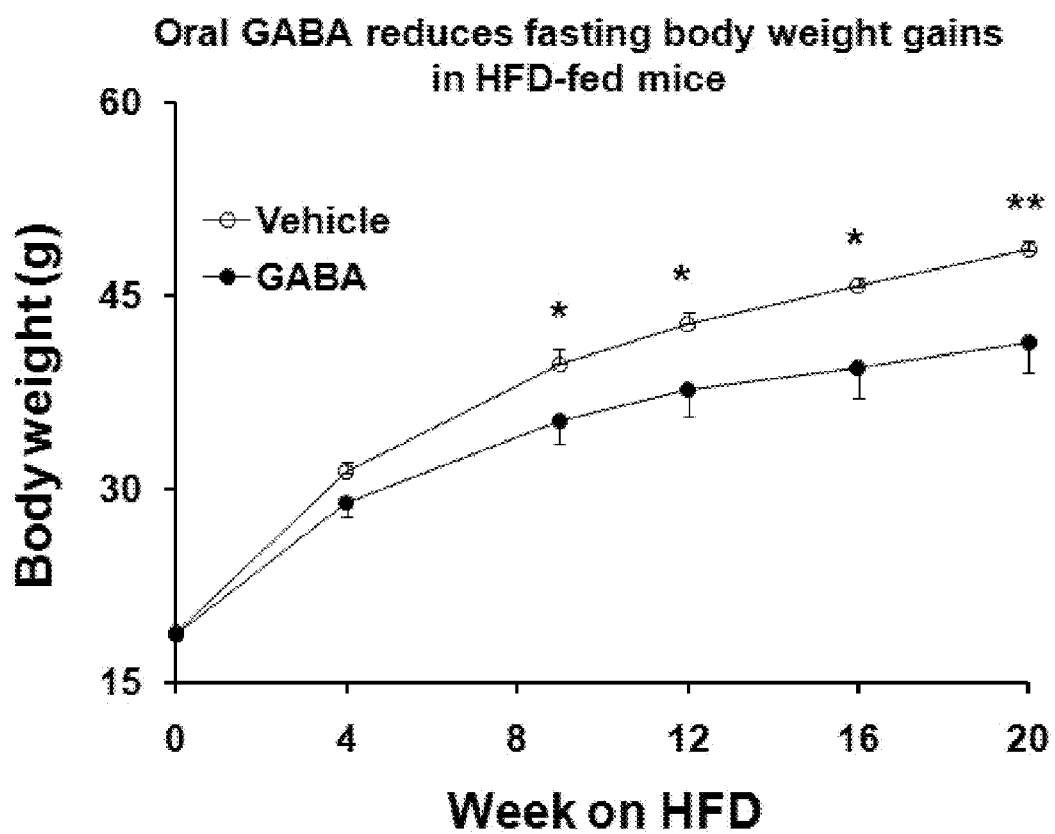
FIG. 6 illustrates fasting body weight—GABA treatment on HFD.
Figure 7:
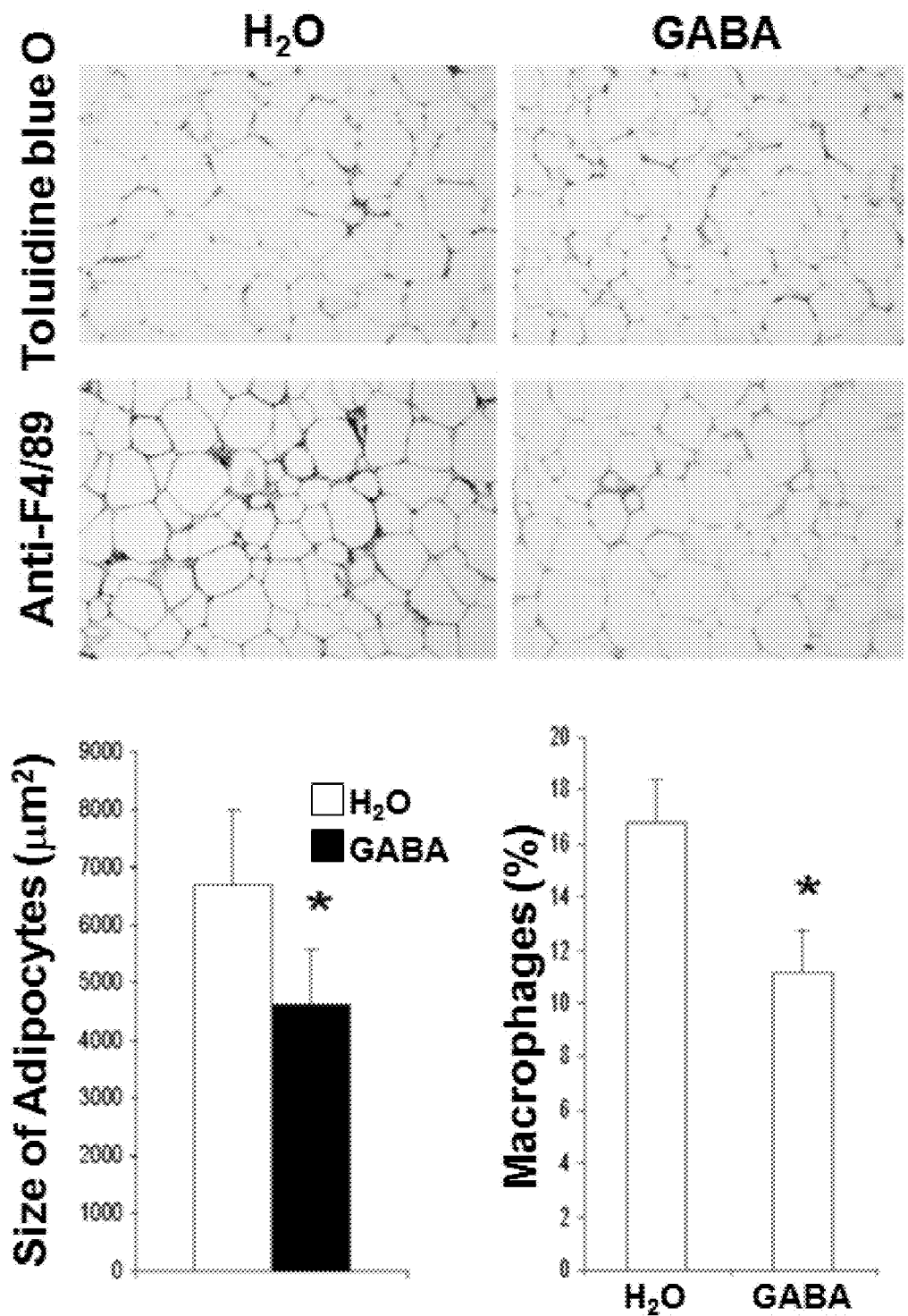
FIG. 7 shows that GABA inhibits the infiltration of macrophages into white adipose tissue (top panel) and that GABA treatment significantly reduces the mass of adipocytes (bottom panel).
Figure 8A:
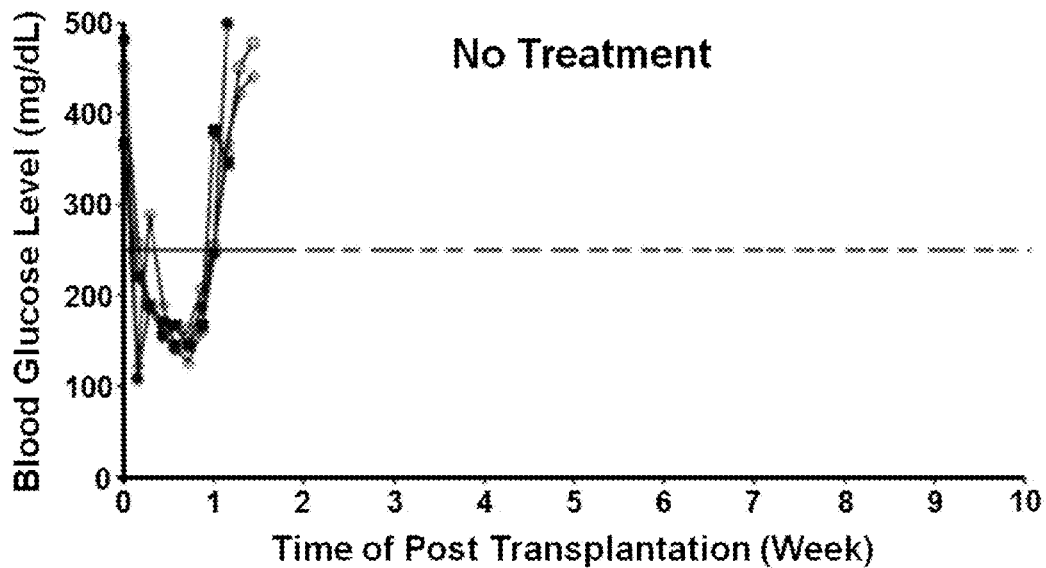
FIGS. 8A-8D show blood glucose levels of mice after receiving islet transplants.
Figure 8B:
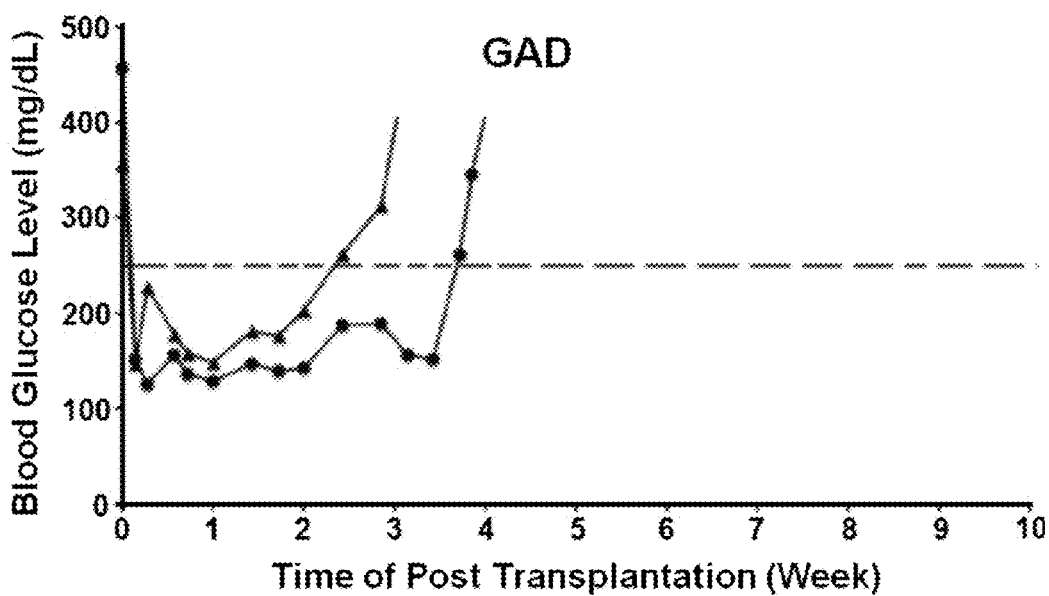
Figure 8C:
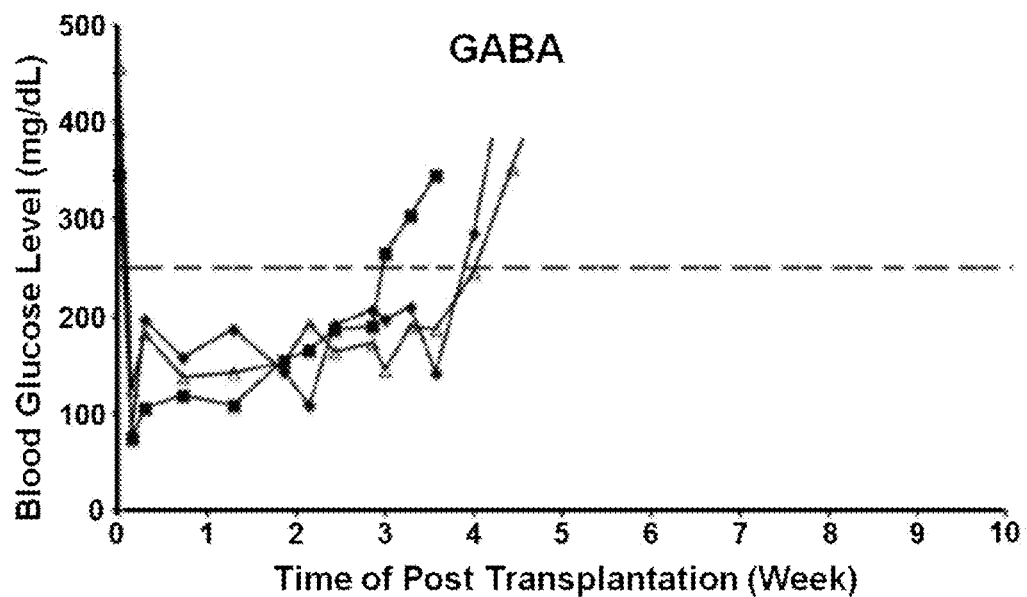
Figure 8D:
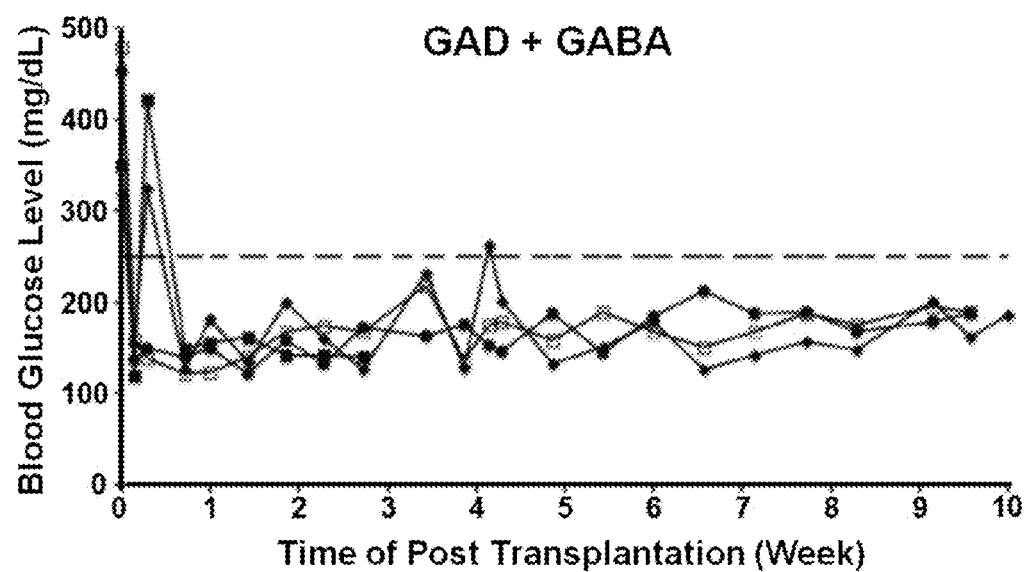

It was observed that there were no differences in the amount of food and water consumed by both experimental and control groups (FIGS. 1 and 2). However, it was also found that:

1) GABA improved glucose tolerance in HFD-fed mice (FIG. 3);

2) GABA improved insulin sensitivity in HFD-fed mice (FIG. 4);

3) GABA reduced fasting blood glucose levels in HFD-fed mice (FIG. 5);

4) GABA mitigated the HFD-induced obesity (body weight) (FIG. 6);

5) GABA inhibited the infiltration of macrophages into white adipose tissue (FIG. 7, top panel); and 6) GABA treatment significantly reduced the mass of adipocytes (FIG. 7 bottom panel).

Example 2

Synergistic Effects of Combined GAD/Alum+GABA Treatment to Preserve Syngenic Islet Graft Survival in Diabetic NOD Mice After the onset of hyperglycemia (blood glucose>300 mgs/dL on two consecutive days) mice were, or were not, immunized with GAD/alum and given drinking water that did, or did not, contain GABA for 28 days. Mice were given insulin as needed. After 28 days the mice received NOD.scid islets under their kidney capsule and insulin treatment was discontinued. Data shown are individual mouse blood glucose levels post-transplantation (FIG. 8A-8D). The mice are staggered because they became spontaneously diabetic at different times, we alternated which treatment group they were placed into, and we are still entering mice into the study and monitoring them. Dashed line indicates blood glucose of 250 mgs/dL.

Untreated transplant recipients became diabetic again about 1 week after receiving the graft, as expected. Mice given GAD/alum monotherapy became diabetic again about 3 weeks after receiving the graft. Mice given GABA (alone) become diabetic again about 3 weeks after receiving the islets. Importantly, all mice given GAD/alum+GABA have remained normoglycemic for the 10 week observation period. A previous study of combination EGF+gastrin which used the same model of syngenic islet transplantation in diabetic NOD mice observed that the median time to recurrence of hyperglycemia was about 8 weeks (Suarez-Pinzon and Rabinovitch (2008) *Transplant Proc.*, 40: 529-532). All GAD+GABA-treated islet recipients have remained normoglycemic longer than that.

Example 3

GAD+GABA Reverses Hyperglycemia in Newly Diabetic NOD Mice

Figure 9A:
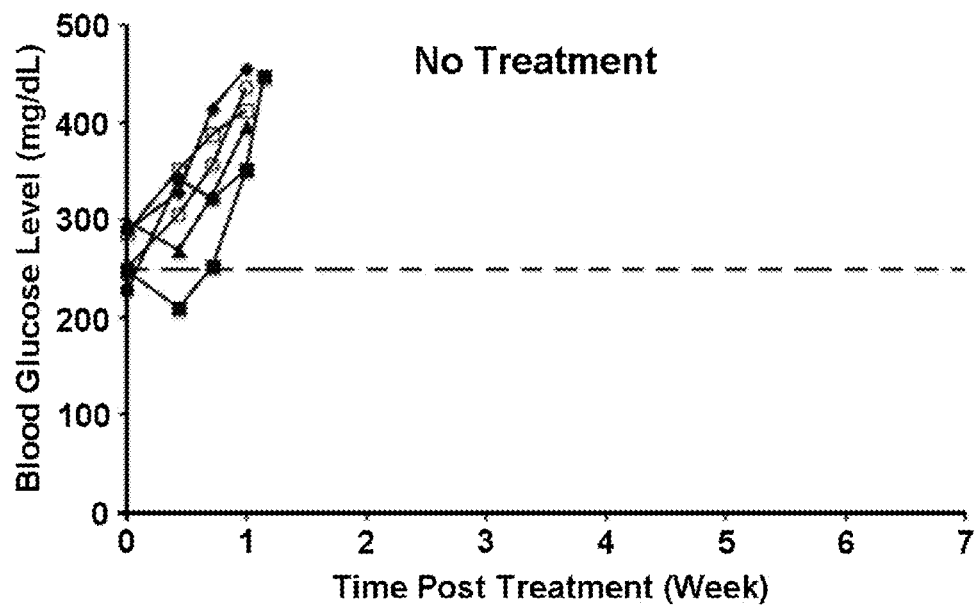
FIGS. 9A-9C illustrate the ability of coadministered GAD and GABA to reverse hyperglycemia in newly diabetic NOD mice. Mice were considered diabetic after two blood glucose>250 mgs/dL. Antigen-based therapy using GAD, insulin B-chain or HSPp277 monotherapy did not reverse hyperglycemia in newly diabetic NOD mice (data not shown). Data shown are blood glucose levels in individual mice given no treatment (FIG. 9A), GABA alone (6 mgs/ml in drinking water) (FIG. 9B), or GABA+GAD/alum (100 µg sc on day 1 and 14) (FIG. 9C). The mice are staggered because they became spontaneously diabetic at different times, we alternated which treatment group they were placed into, and we are still entering mice into the study and monitoring them.
Figure 9B:
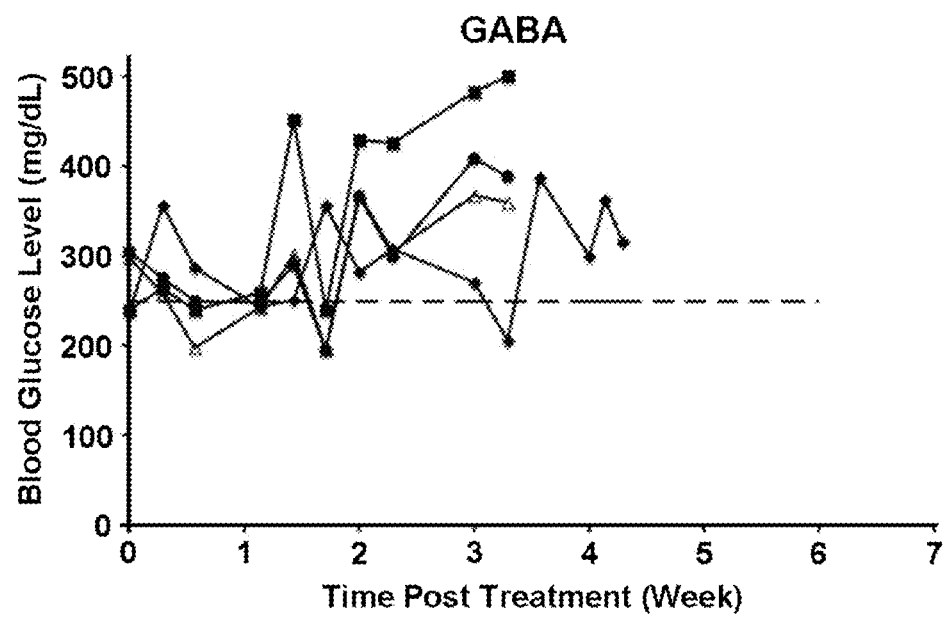
Figure 9C:
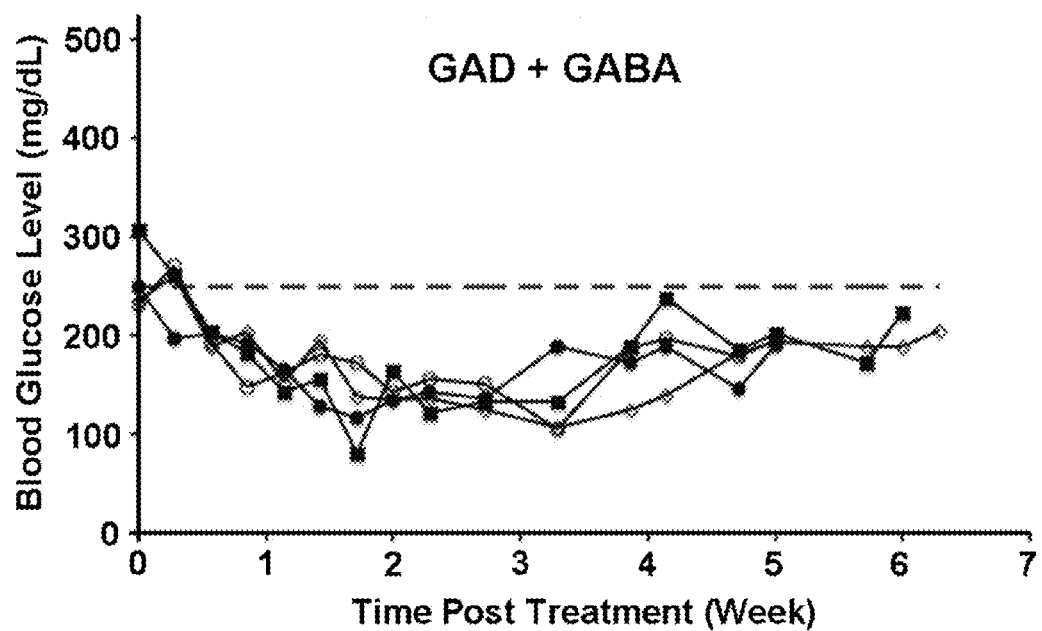

Antigen-based therapy alone (using GAD, insulin B-chain or HSPp277) cannot reverse hyperglycemia in newly diabetic NOD mice. Based on the ability of GAD+GABA therapy to prolong islet graft survival, we tested whether this treatment could reverse hyperglycemia in newly diabetic NOD mice. We are still adding mice into these studies, but the patterns are clear. GABA monotherapy prolongs a state of modest hyperglycemia for a short period, after which the mice progress to severe hyperglycemia. In contrast, hyperglycemia was reversed in all mice that were given GAD+GABA (FIG. 9A-9C). Thus, combination of ABT with GABA had a clear synergistic effect. The efficacy of GAD+GABA treatment is very promising even when compared to combination therapies using much stronger immune modulators e.g., anti-CD3 reversed T1D in about 37%-80% of newly diabetic NOD mice (Sherry et al. (2007) *Endocrinology*, 148: 5136-5144; Chatenoud et al. (1994) *Proc. Natl. Acad. Sci., U.S.A.*, 91: 123-127; Turvey et al. (2005) *J. Clin. Invest.*, 115: 2454-2461), combined anti-CD3+exendin-4 had a 44% remission rate over a 40-70 day observation period (Sherry et al. (2007) *Endocrinology*, 148: 5136-5144), anti-lymphocyte serum (ALG) reversed hyperglycemia in 57% of treated mice over 200 day observation period (Maki et al. (1992) *Proc. Natl. Acad. Sci., U.S.A.*, 89: 3434-3438), ALG+ GCSF reversed T1D in 75% of mice over a 180 day observation period (Parker et al. (2009) *Diabetes*, 58: 2277-2284) and IL-2 reversed T1D in 60% of mice over a 56 day observation period (Grinberg-Bleyer et al. (2010) *J. Exp. Med.*, 207: 1871-1878). Thus GAD+GABA has a synergistic and robust therapeutic effect.

Example 4

GABA can Prevent Oxidative-Stress Induced β-Cell Apoptosis

C57Bl/6 mice received a moderate dose of STZ and then given plain water (control), water+GABA, or water+baclofen (a $GABA_B$-R agonist). 48 hours later their pancreas were removed and sections co-stained with TUNNEL and anti-insulin.

Figure 10A:
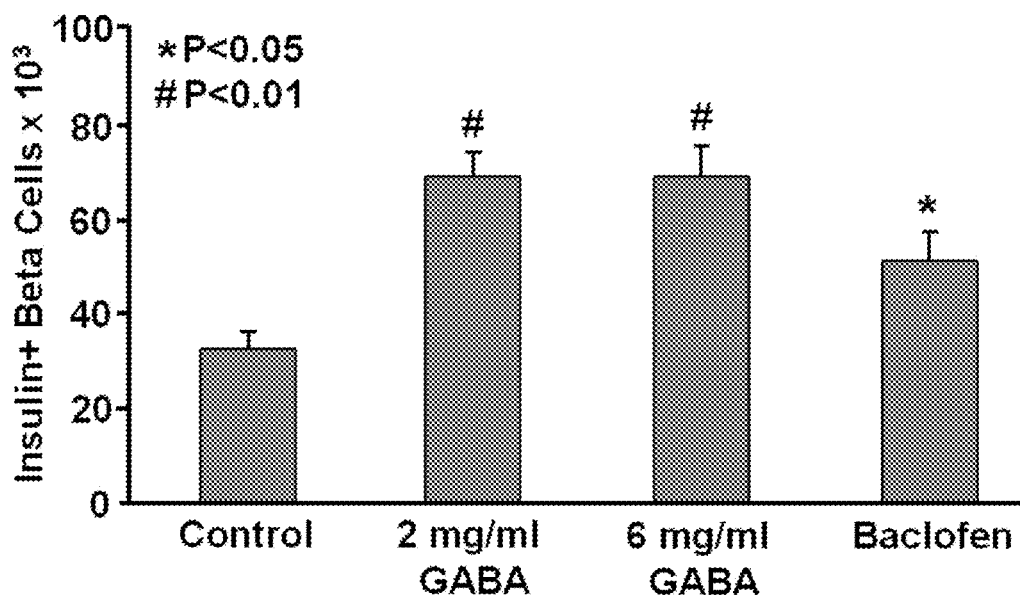
FIGS. 10A-10D show that GABA can prevent oxidative-stress induced β-cell apoptosis.
Figure 10B:
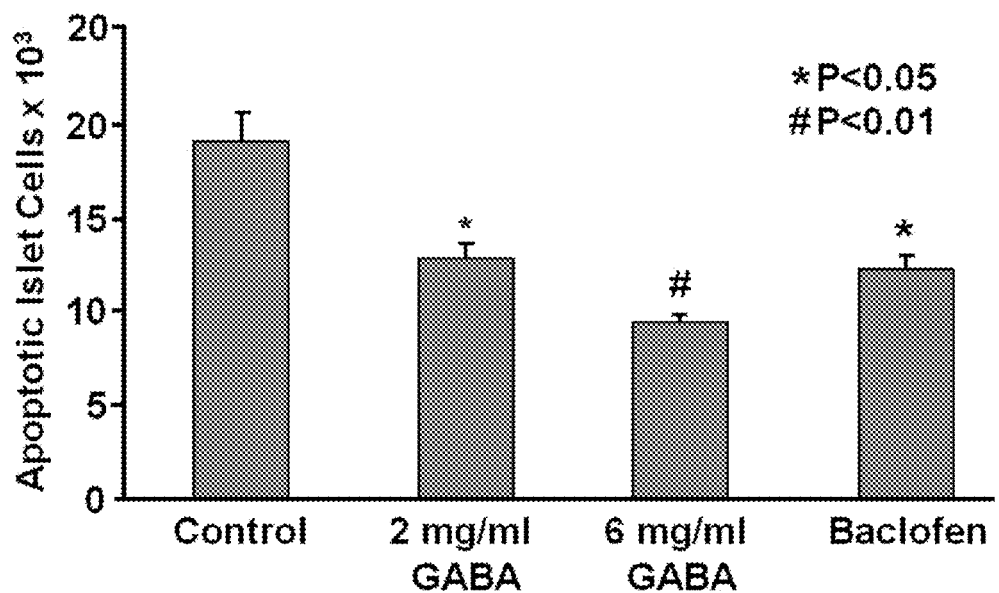

FIG. 10A shows that GABA (both 2 mg/ml and 6 mgs/ml) and baclofen in water significantly inhibits the STZ mediated oxidative-stress-induced apoptosis. *$P<0.05$, #$P<0.01$. N=4 mice/group, at least 100 islets analyzed per group.

FIG. 10 B shows the number of insulin-expressing cells per 100 islet cells. The data indicate that modulation of GABA-R receptors can preserve insulin-producing cells in the islets.

Figure 10C:
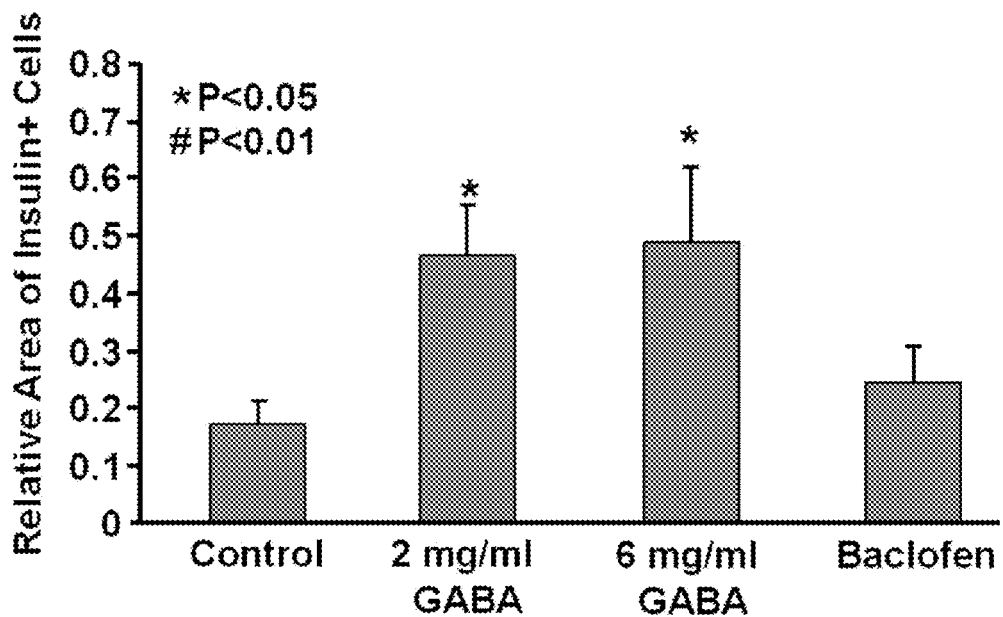

FIG. 10C shows the relative area of insulin+ cells to the total area of the islets. The data again show that GABA treatment preserve the area of insulin producing β-cells. Baclofen treatment also led to greater β-cell area, but this did not reach the level of statistical significance.

Figure 10D:
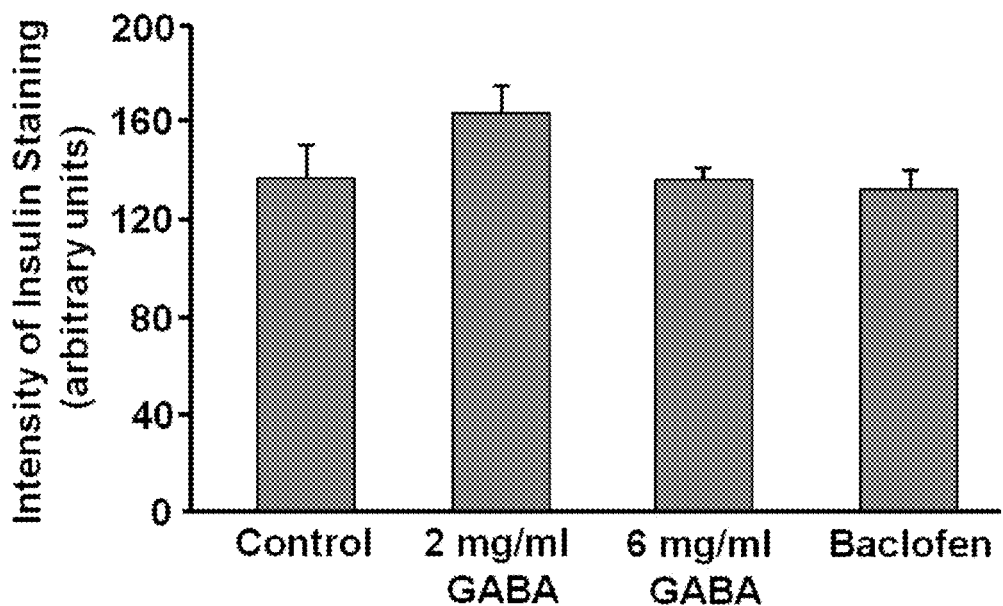

FIG. 10D shows that the intensity of islet insulin staining is similar between groups, which is not unexpected. This means that the β-cells that survive STZ treatment express insulin to the similar extents regardless of the presence or absence of GABA treatment. GABA therefore appears to act mainly at protecting β-cells from apoptosis.

We conclude that modulation of β-cell GABA-Rs can protect them from oxidative stress-induced apoptosis of β-cells, preserving insulin-expressing β-cells in the GABA-treated mice.

Example 5

Cotreatment with GABA Enhances the Ability of IL-2 to Reverse T1D

Figure 11:
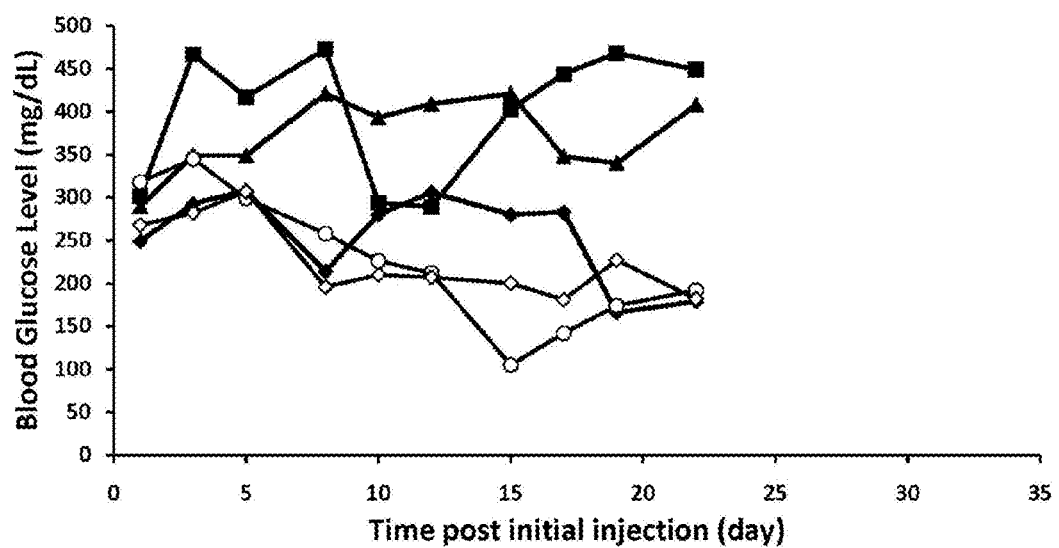
FIG. 11 shows that the effect of cotreatment with GABA and IL-2 on type one diabetes and represented by blood glucose level.

Treatment with IL-2 has been shown to have a modest ability to reverse hyperglycemia in newly diabetic NOD mice. We now have data showing that administration of IL-2 with GABA can enhance its therapeutic effect, and more efficiently reverse hyperglycemia. In the FIG. 11, only one of three newly diabetic NOD mice treated with IL-2 became normoglycemic (blood glucose below 250 mgs/dl) (individual mice represented by black symbols). In contrast two of two newly diabetic mice treated with IL-2+ GABA became normoglycemic (open symbols).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of delaying the onset of type I diabetes, and/or slowing the progression of type I diabetes, and/or reducing the severity of type I diabetes in a mammal, said method comprising coadministering to said mammal:
   a first compound comprising gamma-aminobutyric acid (GABA); and
   a second compound comprising GAD65 or an immunogenic fragment thereof;
   wherein said first compound and said second compound are administered in an amount sufficient to delay the onset of type I diabetes, and/or slow the progression of type I diabetes, and/or reduce the severity of type I diabetes in said mammal.

2. The method of claim 1, wherein said second compound comprises GAD65.

3. The method of claim 1, wherein said second compound comprises an immunogenic fragment of GAD65.

4. A method of delaying the onset of hyperglycemia, and/or slowing the progression of hyperglycemia, and/or reducing the severity of hyperglycemia, said method comprising coadministering to said mammal:
   a first compound comprising gamma-aminobutyric acid (GABA); and
   a second compound comprising GAD65 or an immunogenic fragment thereof;
   wherein said first compound and said second compound are administered in an amount sufficient to delay the onset of hyperglycemia, and/or slow the progression of hyperglycemia, and/or reduce the severity of hyperglycemia in said mammal.

5. The method of claim 4, wherein said second compound comprises GAD65.

6. The method of claim 4, wherein said second compound comprises an immunogenic fragment of GAD65.

7. A method of promoting transplanted islet cell survival in a mammal having Type I diabetes or at risk for type I diabetes who is a recipient of transplanted islet cells, said method comprising coadministering to said mammal:
   a first compound comprising gamma-aminobutyric acid (GABA); and
   a second compound comprising GAD65 or an immunogenic fragment thereof;
   wherein said first compound and said second compound are administered in an amount sufficient to promote transplanted islet cell survival in said mammal.

8. The method of claim 7, wherein said second compound comprises GAD65.

9. The method of claim 7, wherein said second compound comprises an immunogenic fragment GAD65.

10. A method of delaying the onset of an immune response, and/or slowing the progression of an immune response, and/or reducing the severity of an immune response, and/or suppressing an immune response in a mammal, said method comprising coadministering to said mammal:
    a first compound comprising gamma-aminobutyric acid (GABA); and
    a second compound comprising GAD65 or an immunogenic fragment thereof;
    wherein said first compound and said second compound are administered in an amount sufficient to delay the onset of an immune response, and/or slow the progression of an immune response, and/or reduce the severity of an immune response, and/or suppress an immune response in said mammal.

11. The method of claim 10, wherein said second compound comprises GAD65.

12. The method of claim 10, wherein said second compound comprises an immunogenic fragment GAD65.

13. A method of protecting beta-cells in a mammal from oxidative stress induced apoptosis said method comprising coadministering to said mammal:
- a first compound comprising gamma-aminobutyric acid (GABA); and
- a second compound comprising GAD65 or an immunogenic fragment thereof;

wherein said first compound and said second compound are administered in an amount sufficient to partially or fully protect said beta cells from oxidative stress induced apoptosis.

14. The method of claim 13, wherein said second compound comprises GAD65.

15. The method of claim 13, wherein said second compound comprises an immunogenic fragment GAD65.

* * * * *